(12) United States Patent
Lakin et al.

(10) Patent No.: US 7,641,660 B2
(45) Date of Patent: Jan. 5, 2010

(54) METHOD, APPARATUS, AND SYSTEM FOR IMAGE GUIDED BONE CUTTING

(75) Inventors: Ryan Cameron Lakin, Warsaw, IN (US); Garrett Sheffer, Warsaw, IN (US); Jim McKale, Syracuse, IN (US)

(73) Assignee: Biomet Manufacturing Corporation, Warsaw, IN (US)

( * ) Notice: Subject to any disclaimer, the term of this patent is extended or adjusted under 35 U.S.C. 154(b) by 733 days.

(21) Appl. No.: 10/795,891

(22) Filed: Mar. 8, 2004

(65) Prior Publication Data

US 2005/0203531 A1    Sep. 15, 2005

(51) Int. Cl.
*A61B 17/58* (2006.01)
(52) U.S. Cl. .................................................... 606/87
(58) Field of Classification Search ............. 606/86–88, 606/53, 130
See application file for complete search history.

(56) References Cited

U.S. PATENT DOCUMENTS

| | | | |
|---|---|---|---|
| 2,246,936 | A | 6/1941 | Grau |
| 2,255,041 | A | 9/1941 | Anderegg |
| 2,360,572 | A | 10/1944 | Mejean |
| 2,422,950 | A | 6/1947 | Cash |
| 2,650,588 | A | 9/1953 | Drew |
| 2,732,618 | A | 1/1956 | Schwinn |
| 3,016,396 | A | 1/1962 | Irie et al. |
| 3,838,011 | A | 9/1974 | Hagen et al. |
| 4,421,112 | A | 12/1983 | Mains et al. |
| 4,624,673 | A | 11/1986 | Meyer |
| 4,646,729 | A | 3/1987 | Kenna et al. |
| 4,718,413 | A | 1/1988 | Johnson |
| 4,903,536 | A | 2/1990 | Salisbury et al. |
| 4,907,578 | A | 3/1990 | Petersen |
| 4,926,847 | A | 5/1990 | Luckman |

(Continued)

FOREIGN PATENT DOCUMENTS

CA    2 422 950    5/2002

(Continued)

OTHER PUBLICATIONS

*Real-Time Image Segmentation for Image-Guided Surgery*, available at http://splweb.bwh.harvard.edu:8000/pages/papers/warfield/sc98/.

(Continued)

*Primary Examiner*—Eduardo C Robert
*Assistant Examiner*—Mary Hoffman
(74) *Attorney, Agent, or Firm*—Bose McKinney & Evans LLP

(57) ABSTRACT

A system for cutting a bone at a desired location may include an image guided drill cylinder configured to receive either a drill bit to create a bore at a target location on the bone or a pin for insertion into the target location, and a cutting block having a plurality of adjustable guides, each defining a cutting path to guide a cutting instrument, a mounting location configured to attach to the bone at the target location, and a plurality of adjustors for adjusting the position of the guides relative to the target location. The system may further include a tracking instrument for providing image guidance of the adjustments to the positions of the guides.

52 Claims, 13 Drawing Sheets

U.S. PATENT DOCUMENTS

| | | |
|---|---|---|
| 4,945,914 A | 8/1990 | Allen |
| 4,964,861 A | 10/1990 | Agee et al. |
| 4,991,579 A | 2/1991 | Allen |
| 5,016,639 A | 5/1991 | Allen |
| 5,046,375 A | 9/1991 | Salisbury et al. |
| 5,073,044 A | 12/1991 | Egner et al. |
| 5,086,401 A | 2/1992 | Glassman et al. |
| 5,094,241 A | 3/1992 | Allen |
| 5,119,817 A | 6/1992 | Allen |
| 5,129,909 A | 7/1992 | Sutherland |
| 5,142,930 A | 9/1992 | Allen et al. |
| 5,178,164 A | 1/1993 | Allen |
| 5,207,114 A | 5/1993 | Salisbury et al. |
| 5,211,164 A | 5/1993 | Allen |
| 5,222,499 A | 6/1993 | Allen et al. |
| 5,230,338 A | 7/1993 | Allen et al. |
| 5,234,433 A | 8/1993 | Bert et al. |
| 5,236,432 A | 8/1993 | Matsen, III et al. |
| 5,282,803 A | 2/1994 | Lackey |
| 5,282,865 A | 2/1994 | Dong |
| 5,299,288 A | 3/1994 | Glassman et al. |
| 5,303,148 A | 4/1994 | Mattson et al. |
| 5,309,913 A | 5/1994 | Kormos et al. |
| 5,330,534 A | 7/1994 | Herrington et al. |
| 5,342,363 A | 8/1994 | Richelsoph |
| 5,364,402 A | 11/1994 | Mumme et al. |
| 5,388,480 A | 2/1995 | Townsend |
| 5,394,457 A | 2/1995 | Leibinger et al. |
| 5,394,875 A | 3/1995 | Lewis et al. |
| 5,397,329 A | 3/1995 | Allen |
| 5,399,868 A | 3/1995 | Jones et al. |
| 5,408,409 A | 4/1995 | Glassman et al. |
| 5,448,489 A | 9/1995 | Reuben |
| 5,458,645 A | 10/1995 | Bertin |
| 5,514,140 A | 5/1996 | Lackey |
| 5,517,990 A | 5/1996 | Kalfas et al. |
| 5,540,695 A | 7/1996 | Levy |
| 5,551,429 A | 9/1996 | Fitzpatrick et al. |
| 5,562,669 A | 10/1996 | McGuire |
| 5,562,675 A | 10/1996 | McNulty et al. |
| 5,575,794 A | 11/1996 | Walus et al. |
| 5,595,193 A | 1/1997 | Walus et al. |
| 5,601,563 A | 2/1997 | Burke et al. |
| 5,611,802 A | 3/1997 | Samuelson et al. |
| 5,636,255 A | 6/1997 | Ellis |
| 5,649,928 A | 7/1997 | Grundei |
| 5,665,092 A | 9/1997 | Mangiardi et al. |
| 5,676,146 A | 10/1997 | Scarborough |
| 5,676,668 A | 10/1997 | McCue et al. |
| 5,681,320 A | 10/1997 | McGuire |
| 5,682,886 A | 11/1997 | Delp et al. |
| 5,682,890 A | 11/1997 | Kormos et al. |
| 5,683,396 A | 11/1997 | Tokish et al. |
| 5,683,397 A * | 11/1997 | Vendrely et al. .............. 606/88 |
| 5,683,398 A | 11/1997 | Carls et al. |
| 5,693,056 A | 12/1997 | Carls et al. |
| 5,702,486 A | 12/1997 | Craig et al. |
| 5,709,689 A | 1/1998 | Ferrante et al. |
| 5,730,130 A | 3/1998 | Fitzpatrick et al. |
| 5,732,703 A | 3/1998 | Kalfas et al. |
| 5,735,856 A | 4/1998 | McCue et al. |
| 5,749,876 A * | 5/1998 | Duvillier et al. .............. 606/88 |
| 5,766,064 A | 6/1998 | Gasbarro |
| 5,769,789 A | 6/1998 | Wang et al. |
| 5,769,861 A | 6/1998 | Vilsmeier |
| 5,799,055 A | 8/1998 | Peshkin et al. |
| 5,799,099 A | 8/1998 | Wang et al. |
| 5,807,252 A | 9/1998 | Hassfeld |
| 5,853,415 A | 12/1998 | Bertin et al. |
| 5,885,299 A | 3/1999 | Winslow et al. |
| 5,891,034 A | 4/1999 | Bucholz |
| 5,904,691 A | 5/1999 | Barnett et al. |
| 5,916,164 A | 6/1999 | Fitzpatrick et al. |
| 5,925,049 A | 7/1999 | Gustilo et al. |
| 5,935,132 A | 8/1999 | Bettuchi et al. |
| 5,967,982 A | 10/1999 | Barnett |
| 5,980,535 A | 11/1999 | Barnett et al. |
| 5,984,930 A | 11/1999 | Maciunas et al. |
| 5,987,960 A | 11/1999 | Messner et al. |
| 5,997,581 A | 12/1999 | Khalili |
| 5,999,837 A | 12/1999 | Messner et al. |
| 6,002,859 A | 12/1999 | DiGioia et al. |
| 6,007,537 A | 12/1999 | Burkinshaw et al. |
| 6,011,987 A | 1/2000 | Barnett |
| 6,013,081 A | 1/2000 | Burkinshaw et al. |
| 6,021,343 A | 2/2000 | Foley et al. |
| 6,033,410 A | 3/2000 | McLean et al. |
| 6,033,415 A | 3/2000 | Mittelstadt et al. |
| 6,050,724 A | 4/2000 | Schmitz et al. |
| 6,052,477 A | 4/2000 | Wang et al. |
| 6,060,932 A | 5/2000 | Devin |
| 6,069,932 A | 5/2000 | Peshkin et al. |
| 6,081,336 A | 6/2000 | Messner et al. |
| 6,096,082 A | 8/2000 | Stegmuller et al. |
| 6,102,914 A | 8/2000 | Bulstra et al. |
| 6,106,464 A | 8/2000 | Bass et al. |
| 6,120,465 A | 9/2000 | Guthrie et al. |
| 6,161,033 A | 12/2000 | Kuhn |
| 6,162,227 A | 12/2000 | Eckhardt et al. |
| 6,165,177 A | 12/2000 | Wilson et al. |
| 6,167,292 A | 12/2000 | Badano et al. |
| 6,187,018 B1 | 2/2001 | Sanjay-Gopal et al. |
| 6,190,395 B1 | 2/2001 | Williams |
| 6,193,666 B1 | 2/2001 | Ouchi |
| 6,193,758 B1 | 2/2001 | Huebner |
| 6,198,794 B1 | 3/2001 | Peshkin et al. |
| 6,205,411 B1 | 3/2001 | DiGioia, III et al. |
| 6,216,029 B1 | 4/2001 | Paltieli |
| 6,226,548 B1 | 5/2001 | Foley et al. |
| 6,246,900 B1 | 6/2001 | Cosman |
| 6,254,605 B1 | 7/2001 | Howell |
| 6,258,096 B1 | 7/2001 | Seki |
| 6,277,123 B1 | 8/2001 | Maroney et al. |
| 6,285,902 B1 | 9/2001 | Kienzle et al. |
| 6,290,704 B1 | 9/2001 | Burkinshaw et al. |
| 6,298,262 B1 | 10/2001 | Franck et al. |
| 6,322,567 B1 | 11/2001 | Mittelstadt et al. |
| 6,333,971 B2 | 12/2001 | McCrory et al. |
| 6,337,994 B1 | 1/2002 | Stoianovici et al. |
| 6,344,043 B1 | 2/2002 | Pappas |
| 6,351,659 B1 | 2/2002 | Vilsmeier |
| 6,361,506 B1 | 3/2002 | Saenger et al. |
| 6,377,839 B1 | 4/2002 | Kalfas et al. |
| 6,379,391 B1 | 4/2002 | Masini |
| 6,381,485 B1 | 4/2002 | Hunter et al. |
| 6,385,475 B1 | 5/2002 | Cinquin et al. |
| 6,387,100 B1 | 5/2002 | Lindequist |
| 6,402,762 B2 | 6/2002 | Hunter et al. |
| 6,405,072 B1 | 6/2002 | Cosman |
| 6,413,261 B1 | 7/2002 | Grundei |
| 6,424,855 B1 | 7/2002 | Blasche et al. |
| 6,430,434 B1 | 8/2002 | Mittelstadt |
| 6,470,207 B1 | 10/2002 | Simon et al. |
| 6,477,400 B1 | 11/2002 | Barrick |
| 6,478,793 B1 | 11/2002 | Cosman |
| 6,478,799 B1 | 11/2002 | Williamson |
| 6,478,802 B2 * | 11/2002 | Kienzle et al. .............. 606/130 |
| 6,490,475 B1 | 12/2002 | Seeley et al. |
| 6,490,477 B1 | 12/2002 | Zylka et al. |
| 6,491,699 B1 | 12/2002 | Henderson et al. |
| 6,493,574 B1 | 12/2002 | Ehnholm et al. |
| 6,494,913 B1 | 12/2002 | Huebner |
| 6,498,944 B1 | 12/2002 | Ben-Haim et al. |
| 6,499,488 B1 | 12/2002 | Hunter et al. |

| | | |
|---|---|---|
| 6,500,179 B1 | 12/2002 | Masini |
| 6,503,255 B1 | 1/2003 | Albrektsson et al. |
| 6,507,751 B2 | 1/2003 | Blume et al. |
| 6,520,964 B2 | 2/2003 | Tallarida et al. |
| 6,520,969 B2 | 2/2003 | Lambrecht et al. |
| 6,533,455 B2 | 3/2003 | Graumann et al. |
| 6,533,737 B1 | 3/2003 | Brosseau et al. |
| 6,551,325 B2 | 4/2003 | Neubauer et al. |
| 6,554,837 B1 | 4/2003 | Hauri et al. |
| 6,556,857 B1 | 4/2003 | Estes et al. |
| 6,558,391 B2 | 5/2003 | Axelson et al. |
| 6,575,980 B1 | 6/2003 | Robie et al. |
| 6,589,281 B2 | 7/2003 | Hyde et al. |
| 6,595,997 B2 | 7/2003 | Axelson, Jr. et al. |
| 6,610,067 B2 | 8/2003 | Tallarida et al. |
| 6,611,141 B1 | 8/2003 | Schulz et al. |
| 6,711,431 B2 | 8/2003 | Sarin et al. |
| 6,629,978 B2 | 10/2003 | Schulzki et al. |
| 6,674,916 B1 | 1/2004 | Deman et al. |
| 6,694,168 B2 | 2/2004 | Traxel et al. |
| 6,697,664 B2 | 2/2004 | Kienzle et al. |
| 6,711,432 B1 | 3/2004 | Krause et al. |
| 6,718,194 B2 | 4/2004 | Kienzle |
| 6,725,082 B2 | 4/2004 | Sati et al. |
| 6,741,883 B2 | 5/2004 | Gildenberg |
| 6,887,247 B1 * | 5/2005 | Couture et al. ............... 606/96 |
| 2001/0010004 A1 | 7/2001 | Traxel et al. |
| 2001/0012606 A1 | 8/2001 | Unger |
| 2001/0016779 A1 | 8/2001 | Lubinus |
| 2001/0027271 A1 | 10/2001 | Franck et al. |
| 2001/0027272 A1 | 10/2001 | Saito et al. |
| 2001/0036245 A1 | 11/2001 | Kienzle et al. |
| 2001/0037064 A1 | 11/2001 | Shahidi |
| 2001/0053204 A1 | 12/2001 | Navab et al. |
| 2002/0038085 A1 | 3/2002 | Immerz |
| 2002/0055679 A1 | 5/2002 | Sati et al. |
| 2002/0055783 A1 | 5/2002 | Tallarida et al. |
| 2002/0058868 A1 | 5/2002 | Hoshino et al. |
| 2002/0068942 A1 | 6/2002 | Neubauer et al. |
| 2002/0072805 A1 | 6/2002 | Sullivian et al. |
| 2002/0077540 A1 | 6/2002 | Kienzle |
| 2002/0077543 A1 | 6/2002 | Grzeszczuk et al. |
| 2002/0095081 A1 | 7/2002 | Vilsmeier |
| 2002/0133172 A1 | 9/2002 | Lambrecht et al. |
| 2002/0133175 A1 | 9/2002 | Carson |
| 2002/0151894 A1 | 10/2002 | Melkent et al. |
| 2002/0183615 A1 | 12/2002 | Bucholz |
| 2002/0188194 A1 | 12/2002 | Cosman |
| 2002/0191814 A1 | 12/2002 | Ellis et al. |
| 2002/0198448 A1 | 12/2002 | Zuk et al. |
| 2002/0198451 A1 | 12/2002 | Carson |
| 2003/0028196 A1 | 2/2003 | Bonutti |
| 2003/0030170 A1 | 2/2003 | Abe et al. |
| 2003/0042641 A1 | 3/2003 | Abe et al. |
| 2003/0045883 A1 | 3/2003 | Chow et al. |
| 2003/0060702 A1 | 3/2003 | Kuth et al. |
| 2003/0069585 A1 | 4/2003 | Axelson et al. |
| 2003/0069591 A1 | 4/2003 | Carson et al. |
| 2003/0073901 A1 | 4/2003 | Simon et al. |
| 2003/0078669 A1 | 4/2003 | Martin et al. |
| 2003/0105528 A1 | 6/2003 | Shimp et al. |
| 2003/0120276 A1 | 6/2003 | Tallarida et al. |
| 2003/0139669 A1 | 7/2003 | Montegrande |
| 2003/0153923 A1 | 8/2003 | Pinczewski et al. |
| 2003/0171756 A1 | 9/2003 | Fallin et al. |
| 2003/0171757 A1 | 9/2003 | Coon et al. |
| 2003/0176783 A1 | 9/2003 | Hu |
| 2003/0208122 A1 | 11/2003 | Melkent et al. |
| 2003/0212403 A1 | 11/2003 | Swanson |
| 2003/0212405 A1 | 11/2003 | Choi |
| 2003/0225413 A1 | 12/2003 | Sanford et al. |
| 2003/0225456 A1 | 12/2003 | Ek |
| 2004/0030237 A1 | 2/2004 | Lee et al. |
| 2004/0034300 A1 | 2/2004 | Verard et al. |
| 2004/0068179 A1 | 4/2004 | Jutras et al. |
| 2004/0077940 A1 | 4/2004 | Kienzle et al. |
| 2004/0082849 A1 | 4/2004 | Schweikard et al. |
| 2004/0097952 A1 | 5/2004 | Sarin et al. |
| 2004/0111024 A1 | 6/2004 | Zheng et al. |
| 2005/0177169 A1 * | 8/2005 | Fisher et al. .................. 606/88 |

FOREIGN PATENT DOCUMENTS

| | | |
|---|---|---|
| DE | 297 04 393 U | 7/1997 |
| DE | 196 39 615 | 4/1998 |
| DE | 200 16 635 U | 2/2001 |
| EP | 0 649 117 A2 | 4/1995 |
| EP | 0 684 786 B1 | 12/1995 |
| EP | 0 649 117 A3 | 1/1996 |
| EP | 0 832 609 A2 | 4/1998 |
| EP | 0 832 610 A2 | 4/1998 |
| EP | 0 832 611 A2 | 4/1998 |
| EP | 0 832 611 A3 | 9/1998 |
| EP | 0 902 434 B1 | 3/1999 |
| EP | 0 904 735 A2 | 3/1999 |
| EP | 0 832 609 A3 | 6/1999 |
| EP | 0 832 610 A3 | 6/1999 |
| EP | 0 920 838 A2 | 6/1999 |
| EP | 0 904 735 A3 | 11/1999 |
| EP | 0 920 838 A3 | 2/2000 |
| EP | 1 269 924 | 12/2002 |
| GB | 2 246 936 A | 2/1992 |
| JP | 3-16396 | 1/1991 |
| JP | 3-168139 | 7/1991 |
| JP | 7-271963 | 10/1995 |
| WO | WO 95/15714 | 6/1995 |
| WO | WO 96/25086 | 8/1996 |
| WO | WO 97/42898 | 11/1997 |
| WO | WO 99/15097 | 4/1999 |
| WO | WO 99/23956 | 5/1999 |
| WO | WO 99/60939 | 12/1999 |
| WO | WO 00/41626 | 7/2000 |
| WO | WO 02/35454 | 5/2002 |
| WO | WO 03/077101 A2 | 9/2003 |

OTHER PUBLICATIONS

T.C. Kienzle III, et al., *A Computer Assisted Total Knee Replacement Surgical System Using a Calibrated Robot.* Northwestern University. Computer-aided radiation therapy simulation: image intensifier spatial distortion correction for large field of view digital flouroscopy, available at http://www.iop.org/EJ/abstract/0031-9155/43/8/019.

* cited by examiner

METHOD, APPARATUS, AND SYSTEM FOR IMAGE GUIDED BONE CUTTING

FIELD OF THE INVENTION

The present method, apparatus, and system generally relate to surgical removal of portions of bone, and more particularly to facilitating accurate location of a cutting path for guiding a cutting instrument when creating a cut through a portion of a bone.

BACKGROUND AND SUMMARY OF THE INVENTION

As a result of many different physiological conditions, it is often necessary to replace joints in various parts of the body with prosthetic components. Surgical procedures for preparing bones to receive such components typically require precise shaping of portions of the bones. For example, during knee joint replacement surgery, precise resection of the ends of the femur and tibia is necessary to achieve a very close match between the surfaces remaining after removal of portions of the bones, and the mating surfaces of the prostheses. Without such precision mating, the reconstructed knee may result in misalignment (alignment that differs from optimal alignment corresponding to the patient's physical characteristics) of the femur and the tibia. Such misalignment may have a variety of undesirable consequences including discomfort to the patient, reduced mobility, and excessive wear on surfaces of the prostheses.

Cutting guides are commonly used to aid the surgeon by providing a surface across which a cutting instrument is moved to create a planar cut through a bone. Such guides permit the surgeon to achieve increased accuracy as compared to free hand bone shaping. The accuracy of the planar cut, however, is dependent upon accurate placement of the cutting guide. Therefore, it is desirable to provide a system for achieving highly accurate placement of a cutting guide to ensure precision mating between the planar cuts made through a bone and the corresponding surfaces of the prosthetic component.

The present method, apparatus, and system (hereinafter collectively referred to as "the present system") provides, in one embodiment, a drill cylinder having a body that defines a central bore, and an element configured to be detected by an image guidance system to permit image guidance of the drill cylinder to predetermined, target locations on the bone. Using the image guided drill cylinder, the surgeon may monitor on a display the current position and alignment of the drill cylinder body as compared to the target locations, and create bores into the bone at the target locations by inserting a drill bit through the central bore of the body. Alternatively, the surgeon may insert pins through the central bore into the bone at the target locations.

The present system further provides a cutting block having a frame, a guide adjustably connected to the frame, an adjustor connected to the frame, and mounting locations defined by the frame and configured to attach to the bone at the target locations. The mounting locations include either bores for receiving the pins that were inserted into the target locations, or pins for insertion into the bores that were created using the image guided drill cylinder. Accordingly, the cutting block can be accurately placed on the bone at the target locations, which in turn accurately places the guide.

The guide defines a cutting path through which a cutting instrument is passed to create a planar cut in the bone. The position of the guide (and the cutting path) relative to the mounting locations is adjustable using the adjustor. Depending upon the embodiment, actuation of the adjuster causes linear or angular adjustment of the position and/or orientation of the cutting path relative to the mounting locations.

Additionally, the present system may include a tracking instrument having an element configured to be detected by the image guidance system and an engagement portion configured to engage the cutting path to permit image guided adjustment of the cutting path. Thus, in addition to providing accurate placement of the cutting path using the image guide drill cylinder to locate the mounting locations of the cutting block, the present system enables the surgeon to achieve even greater accuracy by providing image guided adjustment of the cutting path when the cutting block is mounted to the bone.

Additional features of the present system will become apparent and be further understood upon reading the detailed description provided below with reference to the following drawings.

DETAILED DESCRIPTION OF EXEMPLARY EMBODIMENTS

Figure 1:
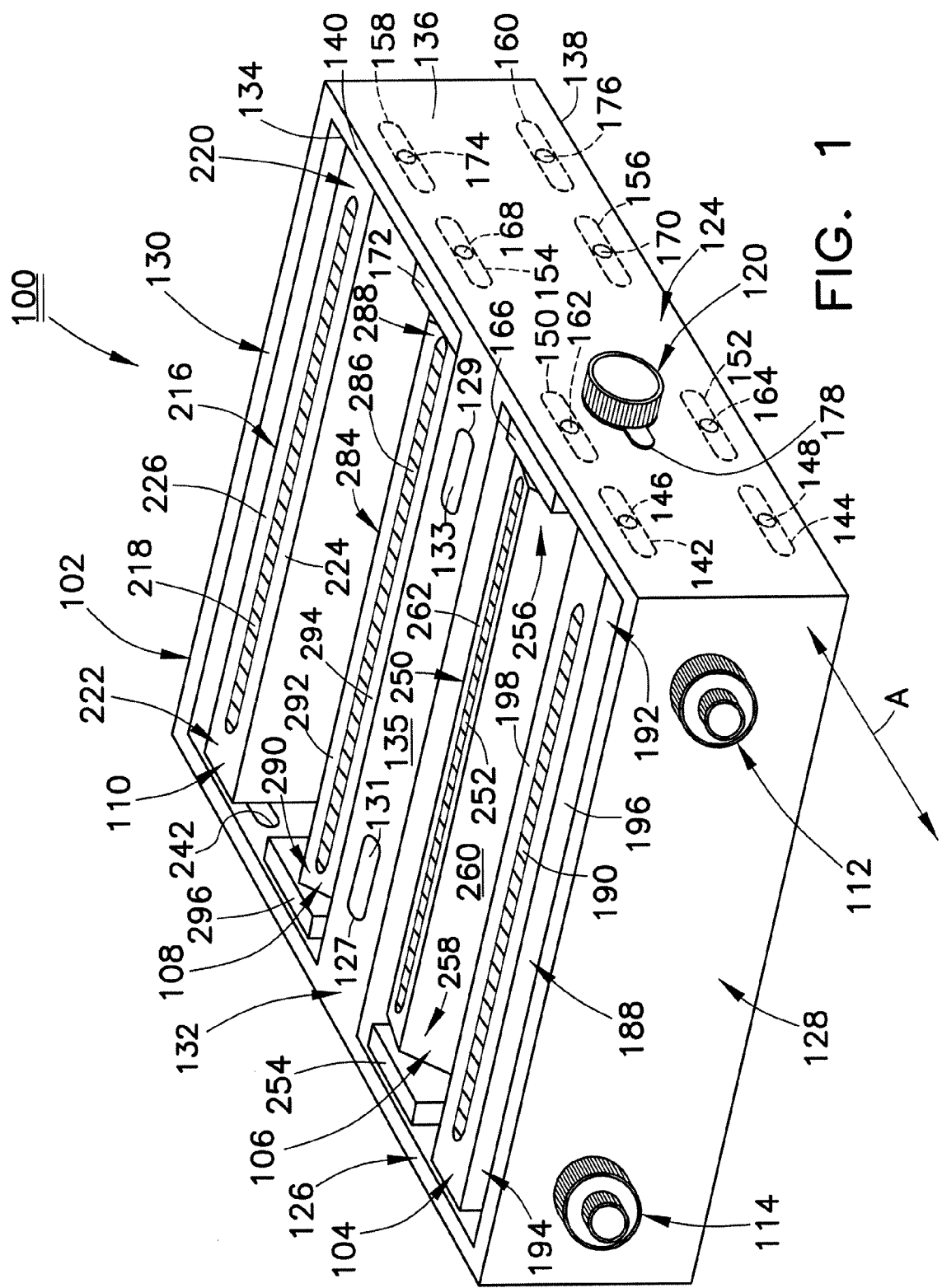
FIG. 1 is a perspective view of one embodiment of a cutting block for use with the present system.

While the present system is susceptible to various modifications and alternative forms, exemplary embodiments thereof have been shown by way of example in the drawings and will herein be described in detail. It should be understood, however, that there is no intent to limit the system to the particular forms disclosed, but on the contrary, the intention is to address all modifications, equivalents, and alternatives falling within the spirit and scope of the system as defined by the appended claims.

Figure 2:
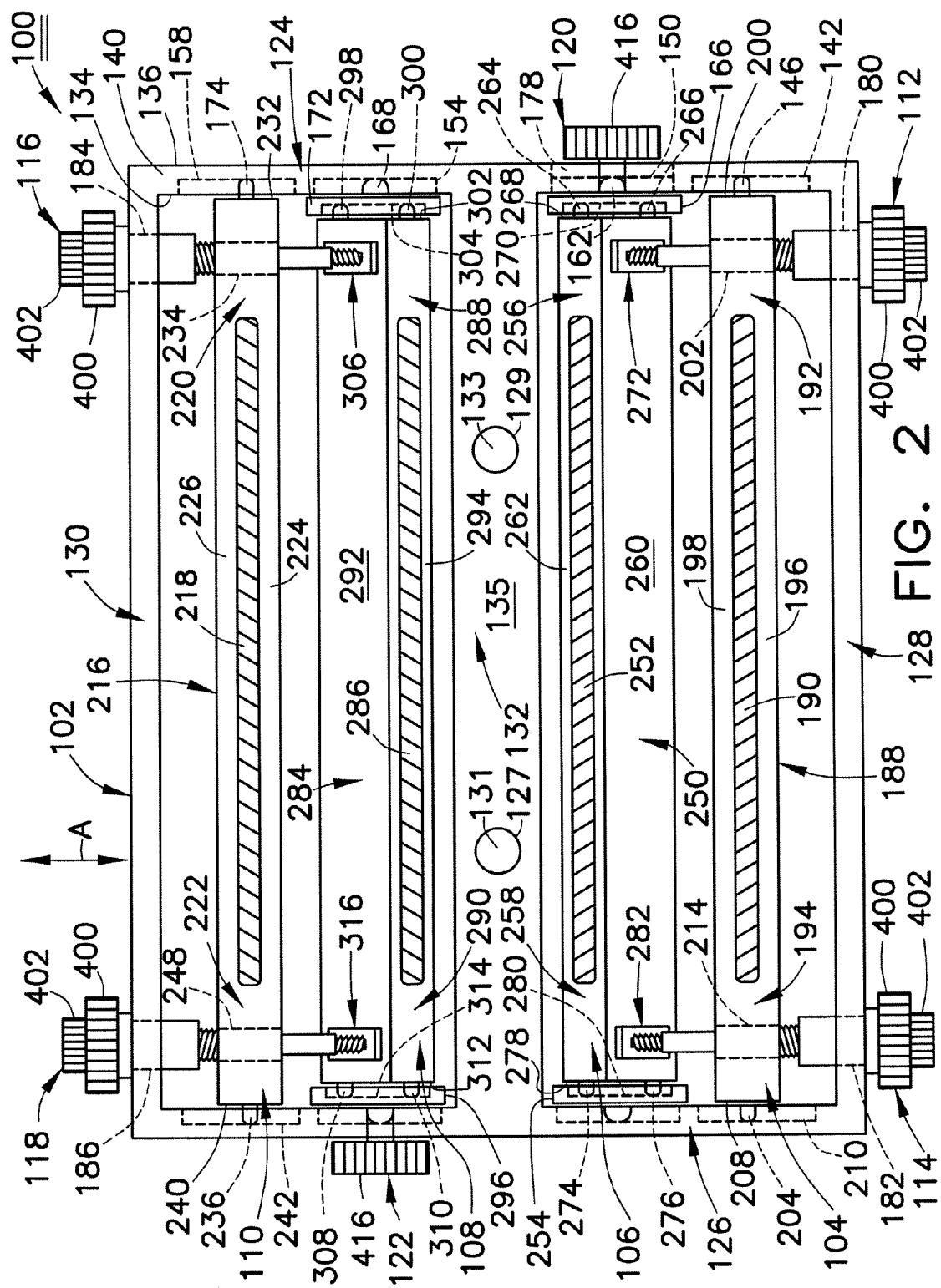
FIG. 2 is a top, plan view of the cutting block of FIG. 1.
Figure 3:
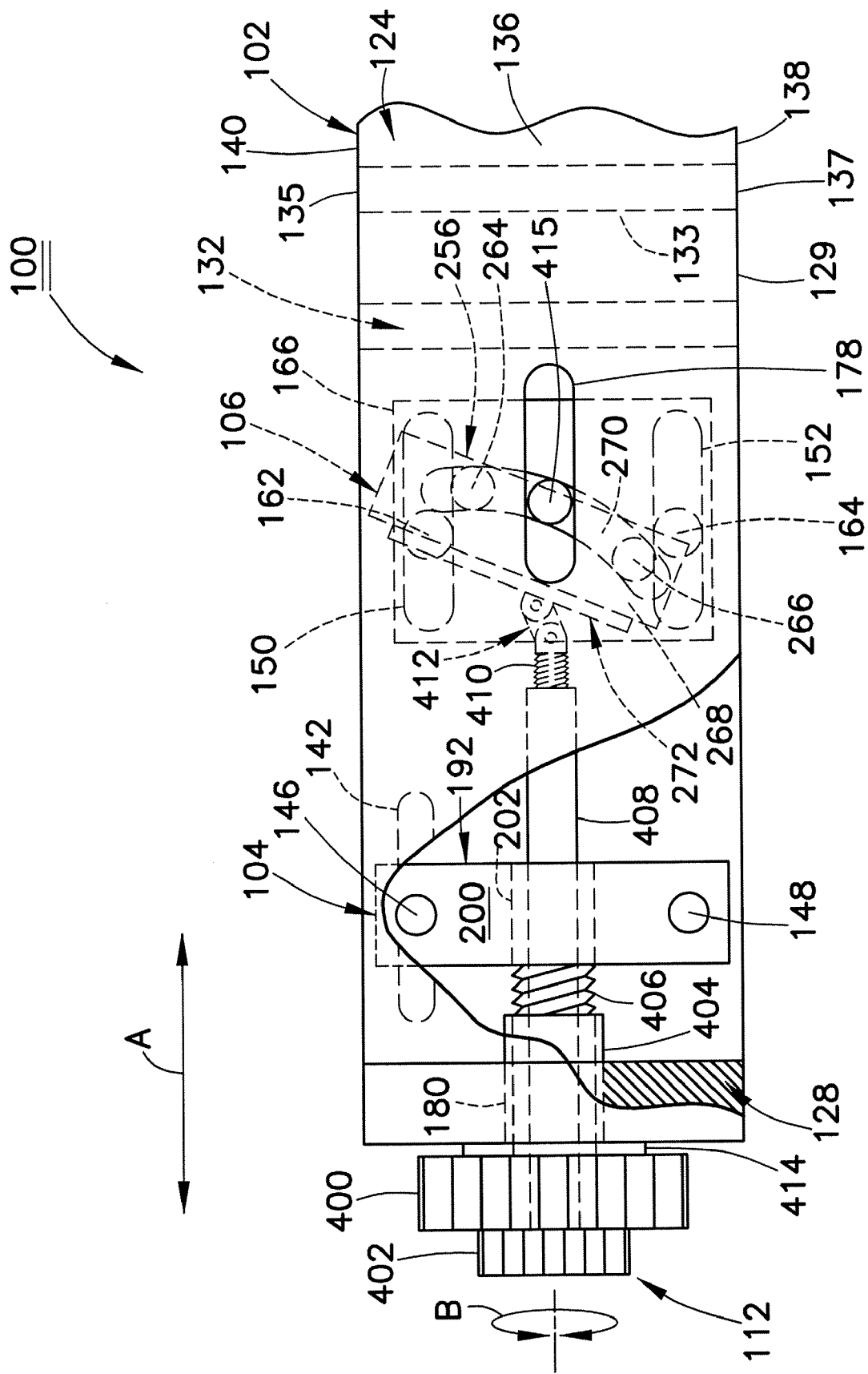
FIG. 3 is a partially fragmented, side elevation view of a portion of the cutting block of FIG. 1.

Referring now to FIGS. 1-3, one embodiment of a cutting block 100 for use in the present system is shown. Cutting block 100 generally includes a frame 102, four adjustable guides 104, 106, 108, 110, four linear adjustors 112, 114, 116, 118, and two angular adjustors 120, 122. It should be understood that the number of guides and adjustors may be different from the number described herein. More specifically, one skilled in the art could readily adapt the teachings of this disclosure to provide a cutting block with one, two, three, or more than four guides with a corresponding number of linear and angular adjustors to position the guides as taught herein. For example, a single guide may be provided that is adjustable within frame 102 into four different positions for making each of the bony cuts described below. In this instance, the single guide would be adjustable linearly and angularly as will become apparent from the following description of embodiments of the system. Alternatively, a pair of guides may be used, such as guides 104, 110, each being adjustable linearly and angularly. Of course, three linearly adjustable guides may be used in a different embodiment, wherein one or more of the guides is also angularly adjustable.

Additionally, it should be understood that while the following description discusses, for example, linear adjustors configured to adjust the position of one end of two guides, separate linear adjustors may be used for each guide. Each of the separate linear adjustors may be configured to adjust both ends of the guide corresponding to the adjustor. Moreover, the described combined adjustor may readily be adapted to adjust both ends of both guides, or both ends of one guide and one end of the other guide. Finally, the described angular adjustors may readily be configured by one skilled in the art to simultaneously adjust the angle of orientation of two or more guides. These and other variations of the guide/adjustor configuration are contemplated by this disclosure and encompassed by the appended claims.

In one embodiment of the present system, frame 102 of cutting block 100 includes a pair of parallel side walls 124, 126 and a pair of parallel end walls 128, 130 that extend substantially perpendicular to side walls 124, 126 to form the substantially rectangular perimeter of frame 102 shown in the Figures. While a rectangular configuration is shown in the Figures, frame 102 may be provided in any configuration suitable for supporting guides 104-110 and accommodating their adjustment. An attachment wall 132 also extends perpendicularly between side walls 124, 126 at a location between end walls 128, 130. Attachment wall 132 may alternatively be replaced by a pair of extensions (one from side wall 124 and one from side wall 126), or omitted in an embodiment wherein side walls 124, 126 or end walls 128, 130 are adapted to facilitate attachment of frame 102 to the target bone. In the illustrated embodiment, attachment wall 132 includes two mounting locations 127, 129, which in the embodiment shown, are occupied by two bores 131, 133, respectively, that extend from an upper surface 135 of attachment wall 132 to a lower surface 137 of attachment wall 132. As is further described below, bores 131, 133 may function as drill guides during attachment of cutting block 100 to a bone, and receive pins after bores are formed in the bone to secure cutting block 100 to the bone. Alternatively, the pins may be placed percutaneously as part of a minimally invasion surgery (MIS) procedure, and secured to the bone to receive bores 131, 133 of cutting block 100. In yet another alternative embodiment, as is also described below, mounting locations 127, 129 may instead be occupied by a pair of pins that extend from lower surface 137 and into bores formed in a bone, thereby securing cutting block 100 to the bone. So long as an adequate connection is provided between cutting block 100 and the target bone, one or more than two of either type of mounting location 127, 129 configuration may be used.

As best shown in FIG. 1, each side wall 124, 126 includes a plurality of travel guides or channels configured to accommodate movement of guides 104-110 during adjustment as further described herein. Since side wall 126 is substantially a mirror image of side wall 124, only side wall 124 is described in detail. Side wall 124 includes an interior surface 134, an exterior surface 136, a lower surface 138, and an upper surface 140. A first upper channel 142 is formed into interior surface 134 and is elongated in direction A as shown in FIG. 1. While each of the plurality of channels is described as being formed into side wall 124, it should be understood that the channels may readily be replaced by ridges that extend inwardly from interior surface 134 to form a pair of guide rails. Alternatively, as will become apparent from the following description, the channels may be replaced with posts or protrusions of some other configuration that extend from interior surface 134 and move within channels or guide rails formed on the corresponding guides 104-110. In yet another alternative embodiment, a single channel or guide rail is provided (on either interior surface 134 or guide 104), and configured to accommodate movement of a single post (on either interior surface 134 or guide 104).

Referring to both FIGS. 1 and 2, in the depicted embodiment, a first lower channel 144 (FIG. 1) is also formed into interior surface 134 of side wall 124, and extends in direction A in substantially parallel relationship to upper channel 142. First upper channel 142 and first lower channel 144 are configured to receive an upper post 146 and a lower post 148, respectively, of adjustable guide 104 as is further described below. Side wall 124 further includes a second upper channel 150, a second lower channel 152, a third upper channel 154, a third lower channel 156, a fourth upper channel 158, and a fourth lower channel 160. Second channels 150, 152 are configured to receive a pair of posts 162, 164, respectively, extending from a mounting plate 166 associated with adjustable guide 106. Similarly, third channels 154, 156 are configured to receive posts 168, 170 of mounting plate 172 associated with adjustable guide 108. Likewise, fourth channels 158, 160 are configured to receive posts 174, 176 of adjustable guide 110. Finally, side wall 124 also includes a slot 178 positioned in substantially parallel relationship between second channels 150, 152. As will become apparent from the description below, slot 178 accommodates movement of angular adjustor 120 when adjustable guide 106 is adjusted in direction A.

End wall 128 includes an opening 180 configured to receive a portion of linear adjustor 112, and an opening 182 configured to receive a portion of linear adjustor 114. Similarly, end wall 130 includes openings 184, 186 configured to receive portions of adjustors 116, 118, respectively.

Guide 104 generally includes a body 188 having at least one surface defining a cutting path 190. In the embodiment shown, cutting path 190 is defined by facing surfaces of a pair of substantially parallel guide walls 196, 198 and is sized to receive the blade of a surgical saw or other cutting instrument (not shown) as is further described below. It should be understood, however, that a single surface of a single guide wall may be used to define any of the cutting paths described herein. Body 188 has a substantially rectangular cross-section and extends substantially the entire distance between interior surfaces 134 of side walls 124, 126. Body 188 includes a first end portion 192, and a second end portion 194, between which extend guide walls 196, 198 to define path 190. First end portion 192 includes spaced apart posts 146, 148 (described above), which extend from an end surface 200 of end portion 192. Additionally, in the embodiment shown, a bore 202 extends through end portion 192 to permit a portion of linear adjustor 112 to extend to guide 106 as is further described below. Second end portion 194 similarly includes a pair of spaced apart posts 204, 206 (only post 204 is shown), which extend from an end surface 208 of end portion 194. Posts 204, 206 also extend into a pair of appropriately spaced channels 210, 212 (only channel 210 is shown) formed in side wall 126 (similar to channels 142, 144 of side wall 124). Finally, end portion 194 also includes a bore 214 (like bore 202 of end portion 192) to permit a portion of adjustor 114 to extend to guide 106 as is further described below.

Guide 110 is substantially identical to guide 104, including all of the same components, in substantially the same configuration. These components include a body 216, a cutting path 218, a first end portion 220, a second end portion 222, and a pair of parallel guide walls 224, 226 having facing surfaces that define cutting path 218. First end portion 220 includes spaced apart posts 174, 176 (described above) extending from an end surface 232, and a bore 234 to receive a portion of adjustor 116. Second end portion 222 also includes a pair of posts 236, 238 (only post 236 is shown) extending from an end surface 240 into a pair of appropriately spaced channels 242, 244 (only channel 242 is shown) formed in side wall 126, and a bore 248 to receive a portion of adjustor 118. Both of guides 104, 110 (and corresponding cutting paths 190, 218) are supported between side walls 124, 126 in a substantially vertical orientation relative to lower surfaces 138 of side walls 124, 126 to guide a surgical saw (not shown) in making bony cuts that are substantially perpendicular to direction A as is further described below.

As best shown in FIG. 2, guide 106 generally includes a body 250 having at least one surface defining a cutting path 252 that receives the blade of a surgical saw (not shown) to create a chamfer cut as is further described below. In the embodiment shown, body 250, like body 188 and body 216, has a substantially rectangular cross-section. Body 250 extends between mounting plate 166 and a similar mounting plate 254 positioned adjacent side wall 126. Body 250 includes a first end portion 256, a second end portion 258, and a pair of parallel guide walls 260, 262 that extend between end portions 256, 258 to define cutting path 252. First end portion 256 includes a pair of spaced apart posts 264, 266, which extend from an end surface 268 of end portion 256 into an arcuate channel 270 formed in mounting plate 166 as is further described below. It should be understood, however, that a pair of arcuate channels (one that receives post 264, and one that receives post 266) may be formed in mounting plate 166. Alternatively, posts 264, 266 may be mounted to mounting plate 166 for cooperation with a corresponding channel (or channels) formed on end surface 268. Moreover, it should be understood that a single post/channel configuration may readily be employed. Any of these alternatives are suitable for use at either end of either of guides 106, 108 so long as they facilitate angular adjustment of cutting paths 252, 286 as described below.

Still referring to the embodiment depicted in FIG. 2, end portion 256 further includes a drive bracket, generally designated by the number 272, which is connected through a linkage to adjustor 112 as is described in greater detail below with reference to FIG. 3. Similarly, second end portion 258 includes a pair of spaced apart posts 274, 276, which extend from an end surface 278 of end portion 258 into an arcuate channel 280 formed in mounting plate 254, and a drive bracket 282, which is connected through a linkage to adjustor 114.

Guide 108 is substantially identical to guide 106, including all of the same components, in substantially the same configuration. The components include a body 284, a cutting path 286, a first end portion 288, a second end portion 290, and a pair of parallel guide walls 292, 294. Body 284 extends between mounting plate 172 and a similar mounting plate 296 positioned adjacent side wall 126. First end portion 288 includes a pair of posts 298, 300, which extend from an end surface 302 into an arcuate channel 304 formed in mounting plate 172, and a drive bracket 306 linked to adjustor 116. Second end portion 290 includes a pair of posts 308, 310, which extend from an end surface 312 into a similar arcuate channel 314 formed in mounting plate 296, and a drive bracket 316 linked to adjustor 118.

Each of linear adjustors 112-118 is substantially identical. Accordingly, only adjustor 112 is described in detail herein with reference primarily to FIG. 3. It should be understood that a variety of different adjustment mechanisms may be employed consistent with the teachings of this disclosure to facilitate adjustment of guides 104-110 in direction A. Adjustor 112 is described as a manually operated, mechanical adjustment mechanism. Alternatively, an electrical adjustment mechanism may be used having a motor or other force-providing device with an actuator (such as a button, switch, etc.) either mounted to frame 102 or remotely located therefrom. It should also be understood that the threaded post and cylinder arrangement described below is merely illustrative, and may readily be replaced with any one of a plurality of different known types of linear adjustment mechanism. Additionally, while adjustment mechanisms that convert rotational motion into linear motion are described below, any other type of suitable mechanism may be used so long as it facilitates adjustment of at least a portion of guides 104-110 (and cutting paths 190, 218, 252, 286) in direction A.

Referring now to FIG. 3, adjustor 112 generally includes a pair of grips 400, 402, a first internally threaded shaft 404, an externally threaded cylinder 406 attached to first end portion 192 of guide 104, a second internally threaded shaft 408, a threaded rod 410, and a linkage 412 attached between threaded rod 410 and drive bracket 272 of guide 106. In the illustrated embodiment, grips 400, 402 are in the form of knobs. It should be understood, however, that grips 400, 402 could readily be formed as plates, sliders, or any other suitable structure configured to cause movement of end portion 192 of guide 104 and end portion 256 of guide 106 in the manner described below. Grip 400 is shown as a large diameter knob, rigidly connected to first internally threaded shaft 404 for rotation therewith in direction B about a central axis of adjustor 112. Grip 400 may be spaced from end wall 128 by a spacer 414. Grip 402 is shown as a smaller diameter knob, rigidly connected to second externally threaded shaft 408, for rotation therewith in direction B. In the illustrated embodiment, grip 402 and shaft 408 rotate independent of grip 400 and shaft 404.

Shaft 404 extends through bore 180 of end wall 128. A conventional retaining mechanism may be used to prevent both grips 400, 402 from moving outwardly, away from end wall 128, while permitting rotation of shafts 404, 408. As should be apparent from FIG. 3, shaft 408 extends with sufficient clearance for rotation through an interior bore (not shown) of shaft 404, an interior bore (not shown) of threaded cylinder 406, and bore 202 through guide 104. Cylinder 406 includes external threads that mate with the internal threads (not shown) of shaft 404. As a result, when grip 400 and shaft 404 are rotated in direction B, cylinder 406 (and guide 104 connected thereto) is moved toward or away from mounting locations 127, 129, depending upon the direction of rotation. As cylinder 406 and guide 104 move, posts 146,148 move within channels 142, 144, respectively, which support guide 104 in the substantially vertical orientation shown in FIG. 3.

Threaded rod 410 similarly includes external threads that mate with the internal threads (not shown) of shaft 408.

Threaded rod 410 is connected to bracket 272 of end portion 256 through linkage 412. Linkage 412 is shown as a pair of pivotal connections which permit tilting of guide 106 (as is further described below). Of course, one of ordinary skill in the art could readily implement any suitable linkage or joint configuration that simultaneously facilitates movement of guide 106 in direction A and tilting of guide 106. As grip 402 and shaft 408 are rotated in direction B, threaded rod 410 is threaded into or out of shaft 408, thereby moving rod 410, linkage 412, and guide 106 toward or away from mounting locations 127, 129, depending upon the direction of rotation. As guide 106 moves, mounting plate 166 also moves, since posts 264, 266 are captured by channel 270 formed in mounting plate 166. Consequently, posts 162, 164 of mounting plate 166 travel within channels 150, 152, respectively, which support mounting plate 166 in the vertical orientation shown in the Figure. Guide 106 is thus maintained in its selected tilted or angular orientation while being moved toward or away from mounting locations 127, 129. It should further be understood that the rod 415 connected to angular adjustor 120 also moves with guide 106. During its travel, rod 415 is guided by slot 178 formed through side wall 124 of frame 102.

Figure 4:
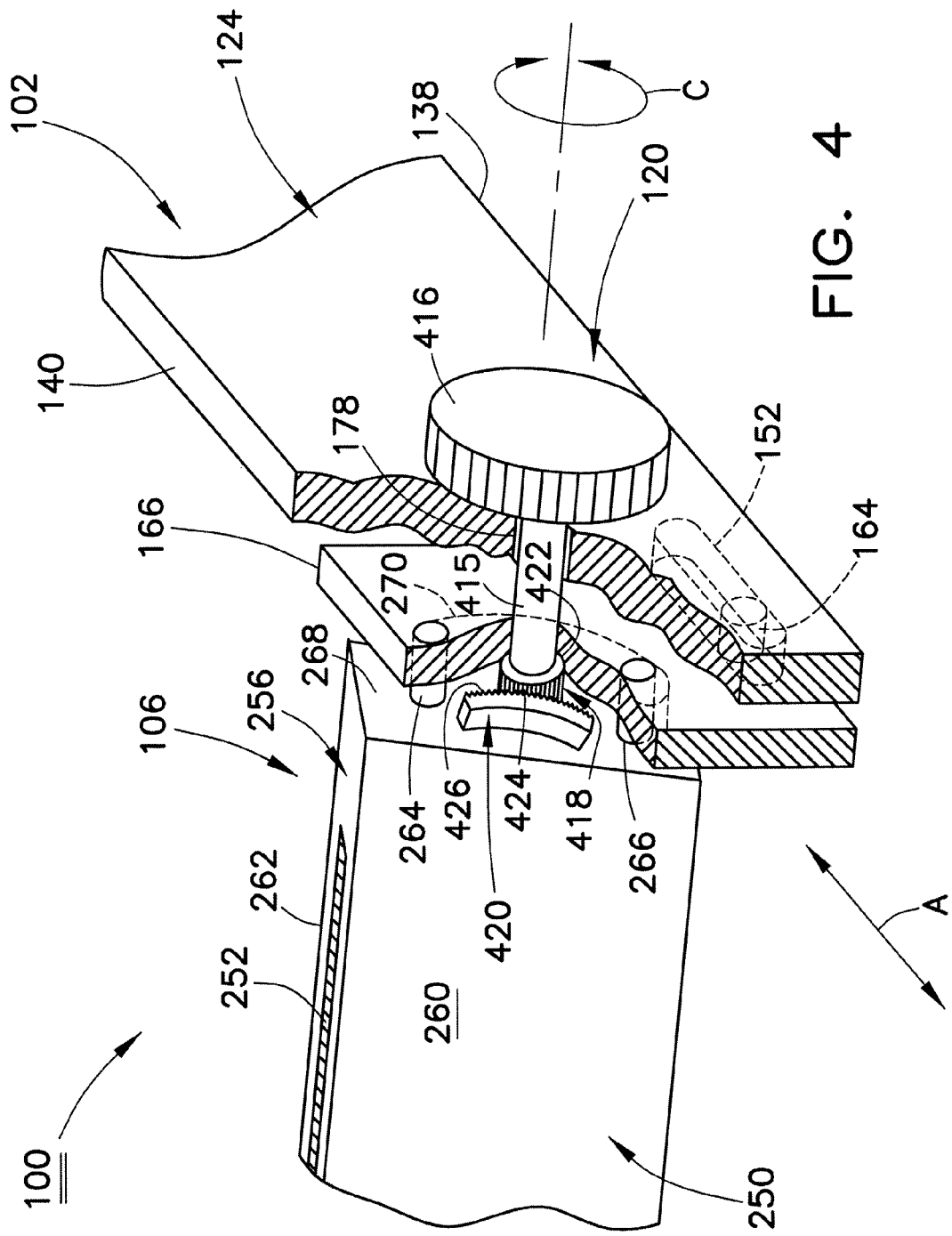
FIG. 4 is a partially fragmented, perspective view of another portion of the cutting block of FIG. 1.

Referring now to FIG. 4, one embodiment of angular adjustor 120 will be described. Since angular adjustors 120, 122 are substantially identical, only angular adjustor 120 is described in detail below. Angular adjustor 120 includes a grip 416 connected to one end of rod 415, a gear 418 connected to the other end of rod 415, and a track 420 connected to end surface 268 of guide 106. As shown, rod 415 extends from grip 416, through slot 178 of side wall 124, through an opening 422 formed through mounting plate 166, and is rigidly connected to gear 418. Gear 418 includes teeth 424. Track 420 is formed such that the teeth 426 of track 420 curve in a manner corresponding to the curve of arcuate channel 270 of mounting plate 166. As should be apparent from the Figure, teeth 424 of gear 418 are positioned in meshing engagement with teeth 426 of track 420.

In operation, grip 416 of angular adjustor 120 is rotated in direction C about a central axis of adjustor 120. As grip 416 rotates, rod 415 rotates, thereby causing rotation of gear 418. As gear 418 rotates, the engagement of teeth 424 and teeth 426 causes guide 106 to move upwardly or downwardly, depending upon the direction of rotation. A portion of the upward or downward movement is translated into a tilt or angular adjustment of the orientation of guide 106 (and cutting path 190) because posts 264, 266 are captured within arcuate channel 270. It should be understood that any suitable locking mechanism may be employed to retain adjustor 120 in position after the orientation of guide 106 has been adjusted. As explained above, the position of guide 106 may also be linearly adjusted using, for example, linear adjustor 112. When linear adjustor 112, which is connected to guide 106 through drive bracket 272 (not shown in FIG. 4), is operated, guide 106, mounting plate 166, and angular adjustor 120 are moved in direction A toward or away from mounting locations 127, 129. During movement in direction A, posts 162, 164 (only post 164 is shown in FIG. 4) move within channels 150, 152 (only channel 152 is shown in FIG. 4), and rod 415 moves within slot 178.

Figure 5:
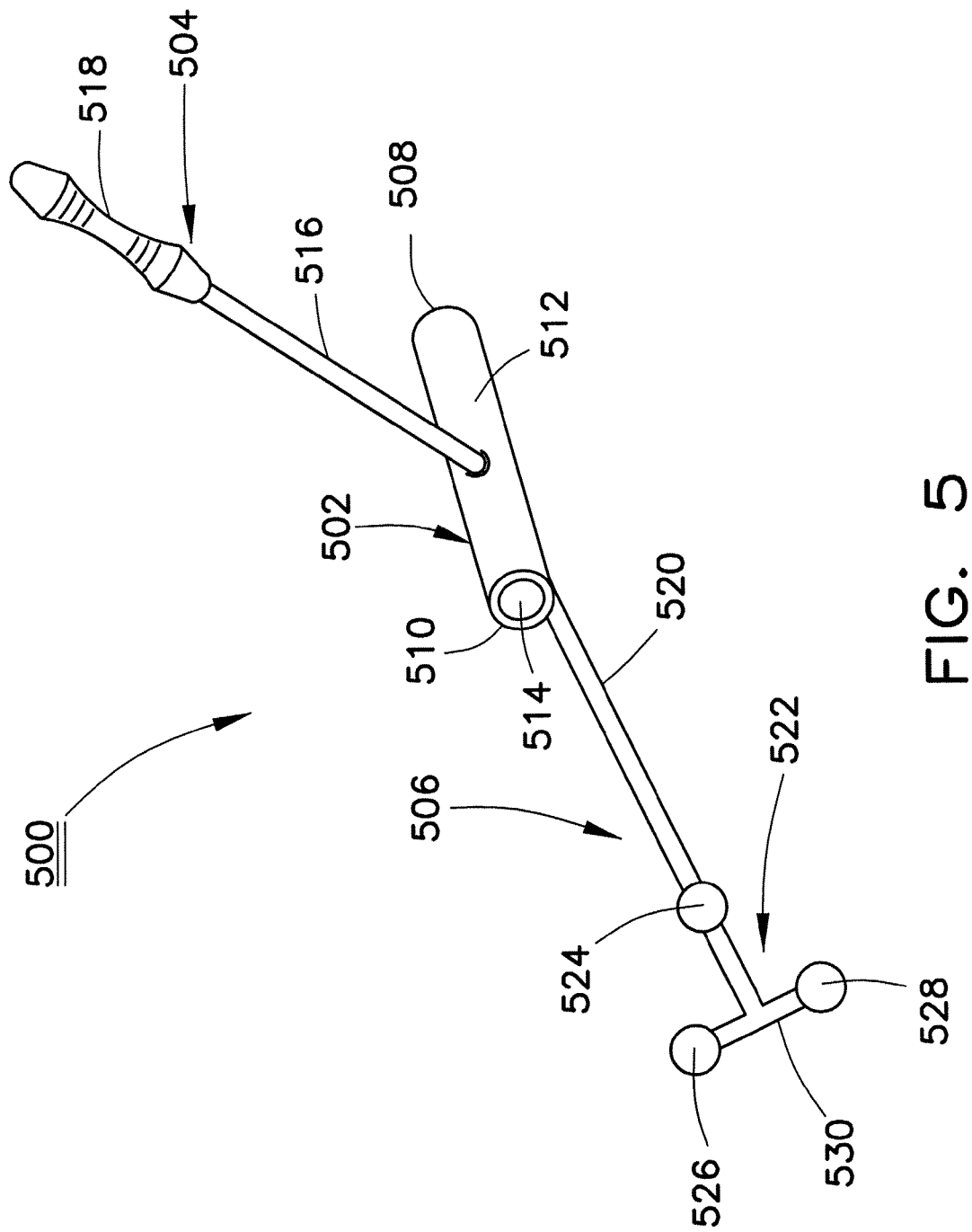
FIG. 5 is a perspective view of one embodiment of a drill cylinder for use with the present system.

Referring now to FIG. 5, one embodiment of an image-guided drill cylinder 500 is shown. Drill cylinder 500 generally includes a body 502, a handle 504, and an image-guidance assembly 506. Body 502 includes a first end 508, a second end 510, and a cylindrical outer wall 512 extending between first and second ends 508, 510 to define a central bore 514. Although outer wall 512 is shown as a solid wall having a substantially constant cross-section, outer wall 512 may instead include openings or open areas and have more than one diameter dimension.

Handle 504 includes a rod 516 and a grip 518. Rod 516 is connected at one end to body 502 of drill cylinder 500, and at the other end to grip 518. It should be understood that the connection between body 502 and rod 516 may be permanent or provide for disconnection of rod 516 (and therefore handle 504). In such an embodiment, handle 504 may be attached to any of a plurality of drill cylinders 500, each having a central bore 514 sized to receive a different size drill bit or fastener, as is further explained below.

Image-guidance assembly 506 includes a shaft 520 connected at one end to body 502 of drill cylinder 500, and at the other end to an array 522 including a plurality of detectable elements 524, 526, 528 connected together by a frame 530. While three detectable elements 524-528 are shown, it should be understood that one, two, or more than three such elements may readily be employed by one skilled in the art, consistent with the teachings of this disclosure. Each detectable element 524-528 is configured to either emit a location signal (e.g., an RF signal, an IR signal, etc.) that is detectable by a receiver as is further described below. Elements 524-528 may utilize passive technology wherein the location signals are only emitted when elements 524-528 are excited by an external source (not shown), or an active technology wherein elements 524-528 emit the location signals so long as a power source (e.g., a battery (not shown)) provides power to elements 524-528. Frame 530 maintains elements 524-528 in fixed relationship to one another. Additionally, the position of array 522 relative to first end 508 of body 502 is also fixed. Thus, by sensing the position of array 522, a conventional image guidance system 808 (described below) may be programmed to determine the precise location of first end 508 of body 502 relative to a fixed reference point as is further described below.

In an alternate embodiment, image-guidance assembly 506 is mounted directly to a drill (not shown) instead of to body 502. In this embodiment, shaft 520 is connected at one end to the drill, and at the other end to array 522. Image-guidance assembly 506 is attached to drill in a known location, such that detection of the position of array 522 enables a determination (by an image guidance system 808 as described below) of the position, relative to a fixed reference point, of an end of the drill bit of the drill, and of the orientation of an axis of the drill bit.

Figure 6:
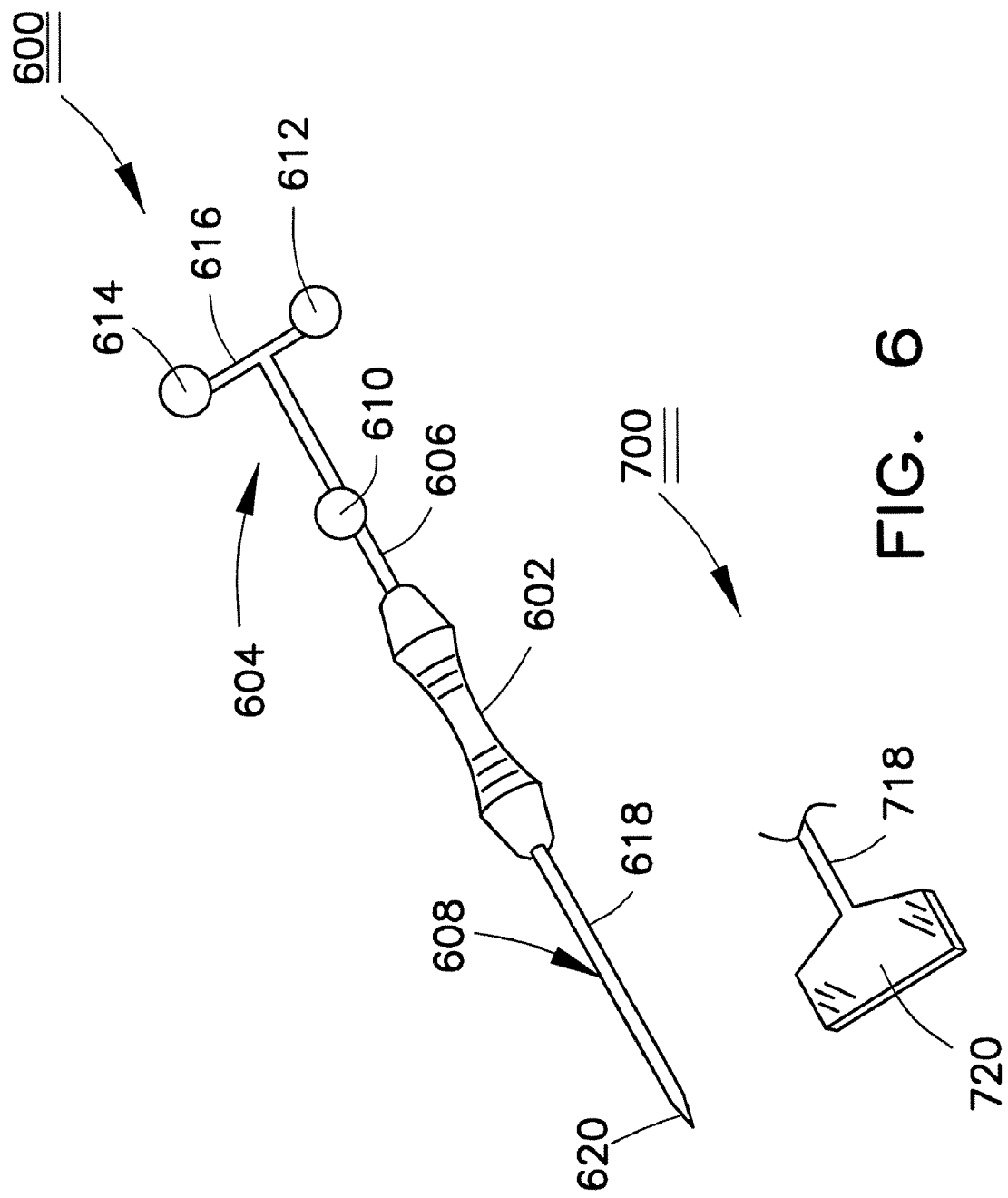
FIG. 6 is a perspective view of embodiments of tracking instruments for use with the present system.

FIG. 6 illustrates two embodiments of tracking instruments for use with the present system. Tracking instrument 600 generally includes a grip 602, an array 604 connected to grip 602 by a shaft 606, and a probe 608. Array 604 is essentially identical to array 522 of drill cylinder 500, including a plurality of detectable elements 610, 612, 614 connected together by a frame 616. Thus, the comments provided above regarding array 522 apply equally to array 604. Probe 608 includes a shaft 618 connected at one end to grip 602, and having at the opposite end an engagement portion or tip 620. As should be apparent from the foregoing, by detecting the position of array 604, image guidance system 808 may be programmed to determine the precise location of tip 620 relative to a reference point since the relative locations of array 604 and tip 620 are fixed.

The tracking instrument 700 shown as the second embodiment in FIG. 6 is substantially identical to tracking instrument 600, except that tip 620 is replaced with an engagement portion formed in the shape of a plate 720 attached to the end of shaft 718. Accordingly, the remaining components of tracking instrument 700 are not shown. As is described in greater detail below, plate 720 is sized to fit within or on cutting paths 190, 252, 286, 218 of guides 104-110, respectively. In this manner, since the relative locations of array 704 (not shown) and plate 720 are known, the precise location of the cutting paths 190, 252, 286, 218 (relative to a reference point) may be determined by image guidance system 808.

Having described the various components of embodiments of the present system, the following portion of the specification discusses examples of applications of the system. For example, the system may be used in a total knee replacement or arthroplasty procedure as described below. It should be understood, however, that the teachings provided herein are also applicable to various other surgical procedures involving removal of portions of bone to, for example, prepare a joint to receive a prosthetic implant.

Figure 7:
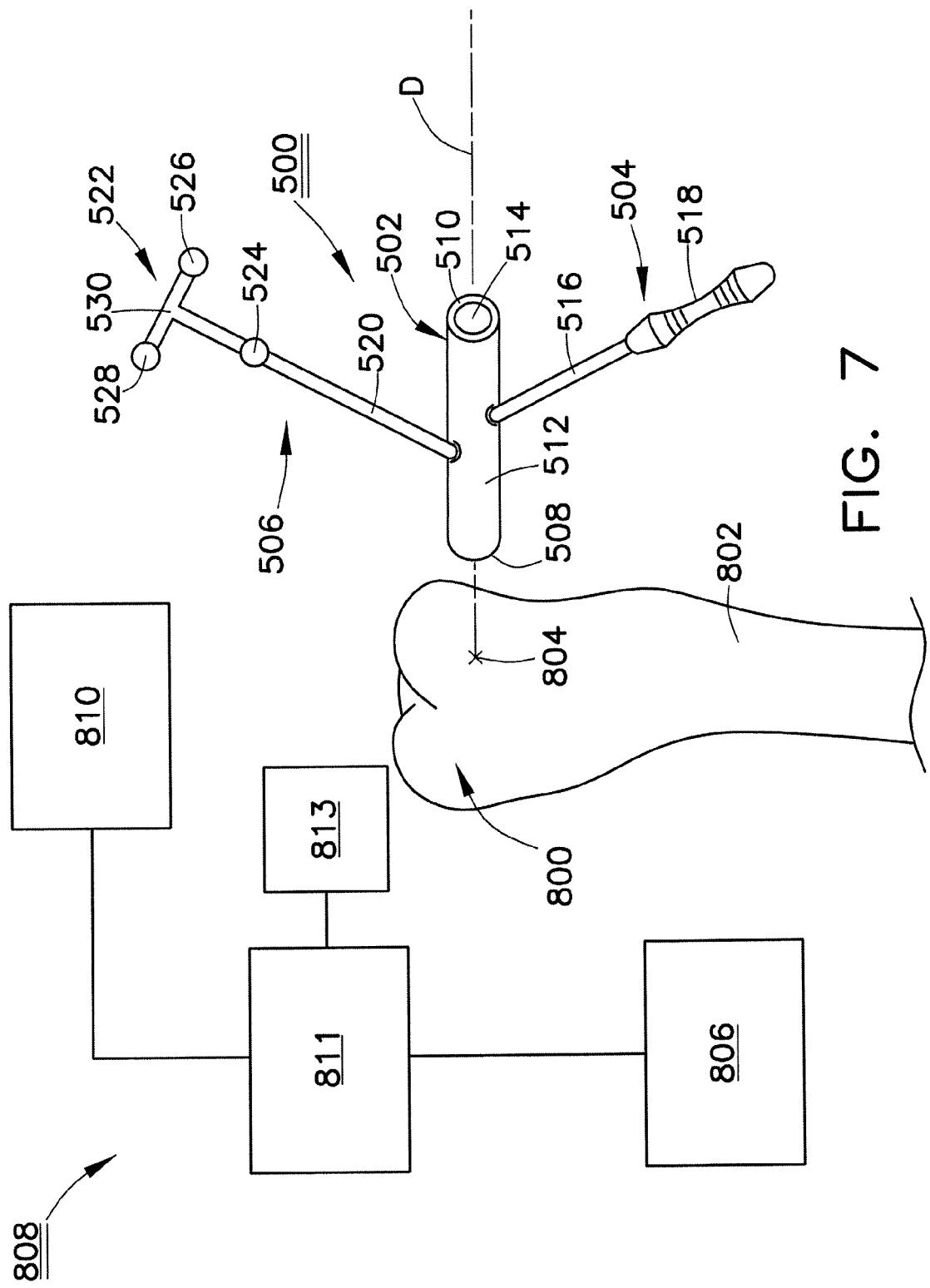
FIG. 7 is a combination of a perspective view of the drill cylinder of FIG. 5 being image guided toward a target location on a bone, and a conceptual diagram of an image guidance system for use with the present system.

If applied in an arthroplasty procedure, the present system facilitates removal of portions of femoral and tibial bone to prepare the bone surfaces for the femoral and tibial prosthetic implants, respectively. First, the distal end of the femur and the proximal end of the tibia are surgically exposed in a conventional manner. The knee joint is then flexed to fully expose the distal end 800 of the femur 802. Referring to FIG. 7, image-guided drill cylinder 500 is next moved by the surgeon into a desired location 804 for placing a headless pin, post, or other similar device (hereinafter referred to as a pin), which in turn locates cutting block 100. While FIG. 7 depicts an entirely exposed bone structure, it should be understood that the pin placement described below may instead be accomplished percutaneously as part of an MIS procedure wherein a small incision is made at the desired pin location, image-guided drill cylinder 500 is placed through the small incision, and a bore is formed for placement of the pin in the manner described below. More specifically, while viewing a visual indication of the three-dimensional orientation of drill cylinder 500 relative to the structure of distal end 800 of femur 802 on a display 806 of an image guidance system 808, the surgeon moves drill cylinder 500 into contact with target location 804 on femur 802 (either directly or through a small incision in the skin), which corresponds to the precise, desired location of one of mounting locations 127, 129. In this example, target location 804 corresponds to the precise, desired location of one of bores 131, 133 of attachment wall 132 of cutting block 100. Image guidance system 808 provides a visual indication on display 806 based on data representing the three-dimensional structure of femur 802, drill cylinder 500, and cutting block 100. A receiver 810 of image guidance system 808 detects the position of elements 524-528 of array 522 connected to body 502 of drill cylinder 500, thereby enabling system 808 to accurately determine the location of first end 508 of body 502 relative to femur 802. In this manner, the surgeon is able to determine not only whether the point of entry of the drill bit (not shown) is accurately located, but whether the angle of entry (represented by axis D of FIG. 7) is appropriate for placement of the pin to be received by cutting block 100.

Once drill cylinder 500 is accurately placed, an appropriately sized pin is placed into central bore 514 of drill cylinder 500 and screwed or otherwise inserted into target location 804 of femur 802. The depth of entry of the pin may be controlled using any of a variety of conventional techniques. After the pin is placed, drill cylinder 500 is removed. It should be understood, however, that instead of placing a pin into femur 802 as described above, drill cylinder 500 may be used to guide a drill bit (not shown) for creating a bore into femur 802. Alternatively, using the embodiment described above wherein array 506 is connected to a drill, the drill may be used directly, under image guidance, to create a bore in target location 804 of femur 802. In either case, the depth of entry of the drill bit may similarly be controlled using any of a variety of conventional techniques. After the bore is created and drill cylinder 500 is removed, an appropriately sized pin may be securely inserted into the bore. The corresponding cutting block 100 in such an embodiment includes bores 131, 133 through attachment wall 132 at mounting locations 127, 129, respectively. Bores 131, 133 are sized to securely receive such pins. As yet another alternative, drill cylinder 500 may be used in the manner described above to create a bore in femur 802 for receiving a pin connected to cutting block 100 at one of mounting locations 127, 129.

Assuming a first pin is placed into femur 802 according to the procedure described above, a second pin may be placed by repeating the procedure, but placing the second pin at a second target location (not shown) that corresponds to a second bore 131, 133 in the known geometry of cutting block 100. After the second pin is inserted into the second target location, drill cylinder 500 is removed. Next, cutting block 100 is positioned onto the first and second pins such that the pins are received by bores 131, 133 formed in attachment wall 132. Any of a plurality of different techniques may be used to secure cutting block 100 to the pins. For example, the pins may include threaded ends that extend from femur 802, through cutting block 100, and project beyond surface 135 of mounting wall 132. The projecting portions of the threaded ends may receive nuts or similar components which may be tightened onto the threaded ends against surface 135. In this manner, cutting block 100 is securely captured in a fixed orientation between the nuts and the femur. Alternatively, cutting block 100 may include set screws or similar components which are controllably inserted into the bores and urged (such as by rotation on internal threads of cutting block 100) into locked engagement with a surface of each pin. Of course, any other connection technique for securely attaching cutting block 100 to the pins is within the scope of the teachings provided herein.

In an alternative embodiment, after the first pin is placed according to the procedure described above, one bore, such as bore 131, of cutting block 100 is placed onto the first pin, but cutting block 100 is not tightly secured to the pin. The second pin may be placed by placing drill cylinder 500 over another bore, such as bore 133, in a predetermined placement location, and rotating cutting block 100 about the first pin until display 806 indicates that drill cylinder 500 is accurately positioned over the second target location on femur 802. After drill cylinder 500 is accurately located, the second pin is simultaneously inserted through drill cylinder 500 (in the manner described above) and bore 133 of cutting block 100. Alternatively, cutting block 100 placed on the first pin may include, or later have attached to it, a tracking instrument (such as instruments 600 or 700) to permit detection of the position of cutting block 100 (more specifically, the location of second bore 133 in cutting block 100). The surgeon may rotate cutting block 100 while viewing the location of second bore 133 on display 806. When second bore 133 is rotated into registration with the second target location on femur 802, the surgeon may secure cutting block 100 to the first pin to fix cutting block 100 in place. Then, a drill or other pin insertion device may be used to insert the second pin through second bore 133 of cutting block 100 and into the second target location of femur 802.

Figure 8:
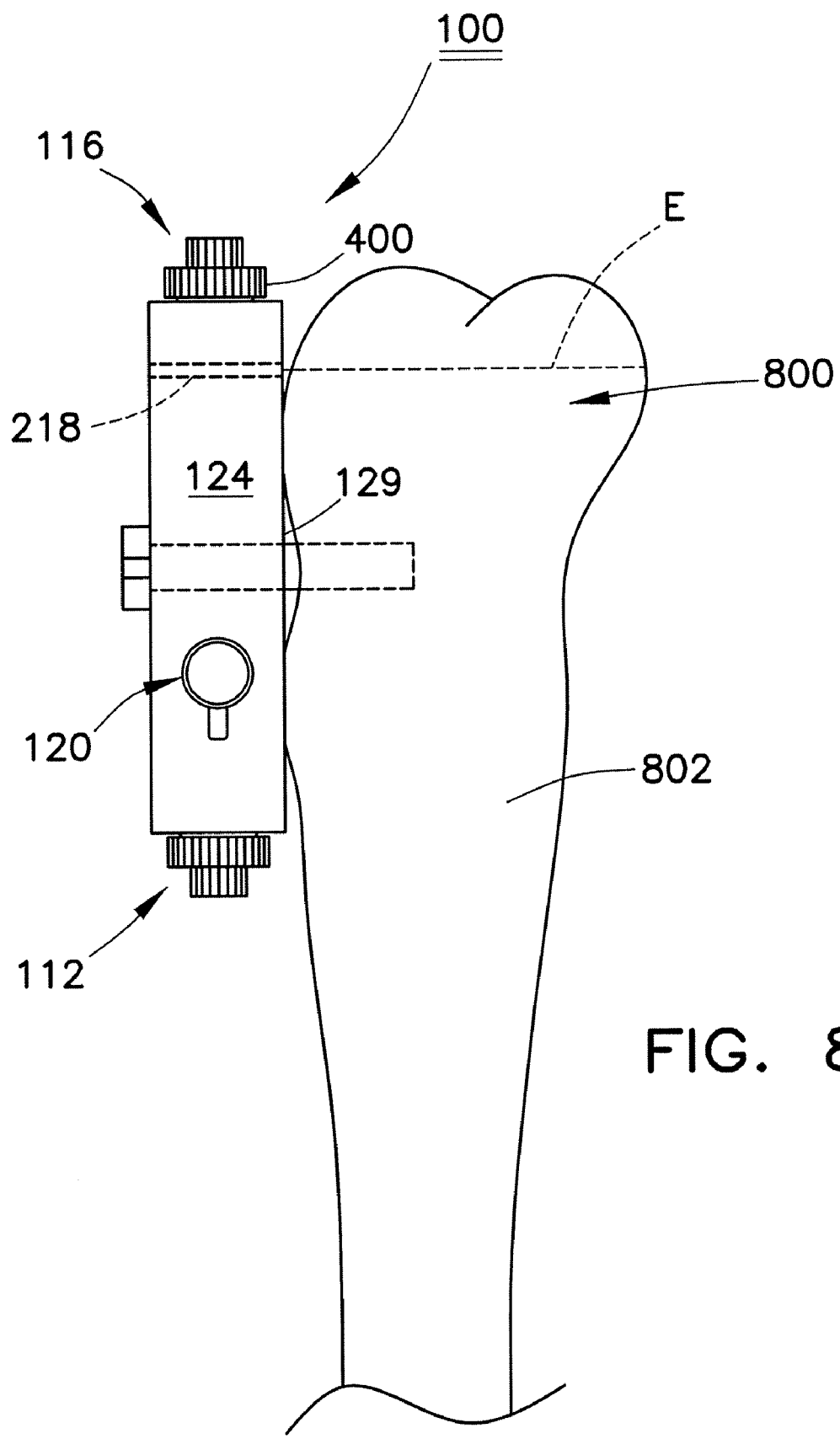
FIG. 8 is a side elevation view of the cutting block of FIG. 1 mounted to a bone in a position to make a distal femoral cut.

After cutting block 100 is secured to the distal end 800 of femur 802 as shown in FIG. 8, the alignment of the cutting path (such as cutting path 218 of guide 110) for creating a first cut (the distal femoral cut) may be adjusted to correspond with the appropriate anterior posterior plane (plane E). To this end, plate 720 of tracking instrument 700 may be inserted into path 218. The surgeon may then rotate grips 400 of adjustors 116, 118 in the manner described above to move end portions 220, 222 of guide 216, respectively, toward or away from mounting locations 127, 129, thereby positioning path 218 such that when a surgical saw is moved along path 218 it will create a surface corresponding to plane E at distal end 800 of femur 802 in the desired orientation, such as substantially perpendicular to the femoral mechanical axis. After plane E is created, cutting block 100 and pins are removed from femur 802.

Alternatively, instead of using tracking instrument 700 (or tracking instrument 600) to provide image guided adjustment of cutting path 218 as described above, plane E may simply be created using cutting block 100 without adjustments to the position of cutting path 218. After plane E is created, the surgeon may position plate 720 of tracking instrument 700 (or tip 620 of tracking instrument 600) onto plane E to verify the location and orientation of plane E by receiving feedback from the image guidance system described below. If plane E is not in a desired location and orientation, the surgeon may adjust the position of cutting path 218 as described above, make a new cut, and verify the accuracy of the cut by again placing plate 720 of tracking instrument 700 (or tip 620 of tracking instrument 600) onto the newly created plane. This iterative process may be repeated until the surgeon is satisfied with the accuracy of the cut.

Figure 9:
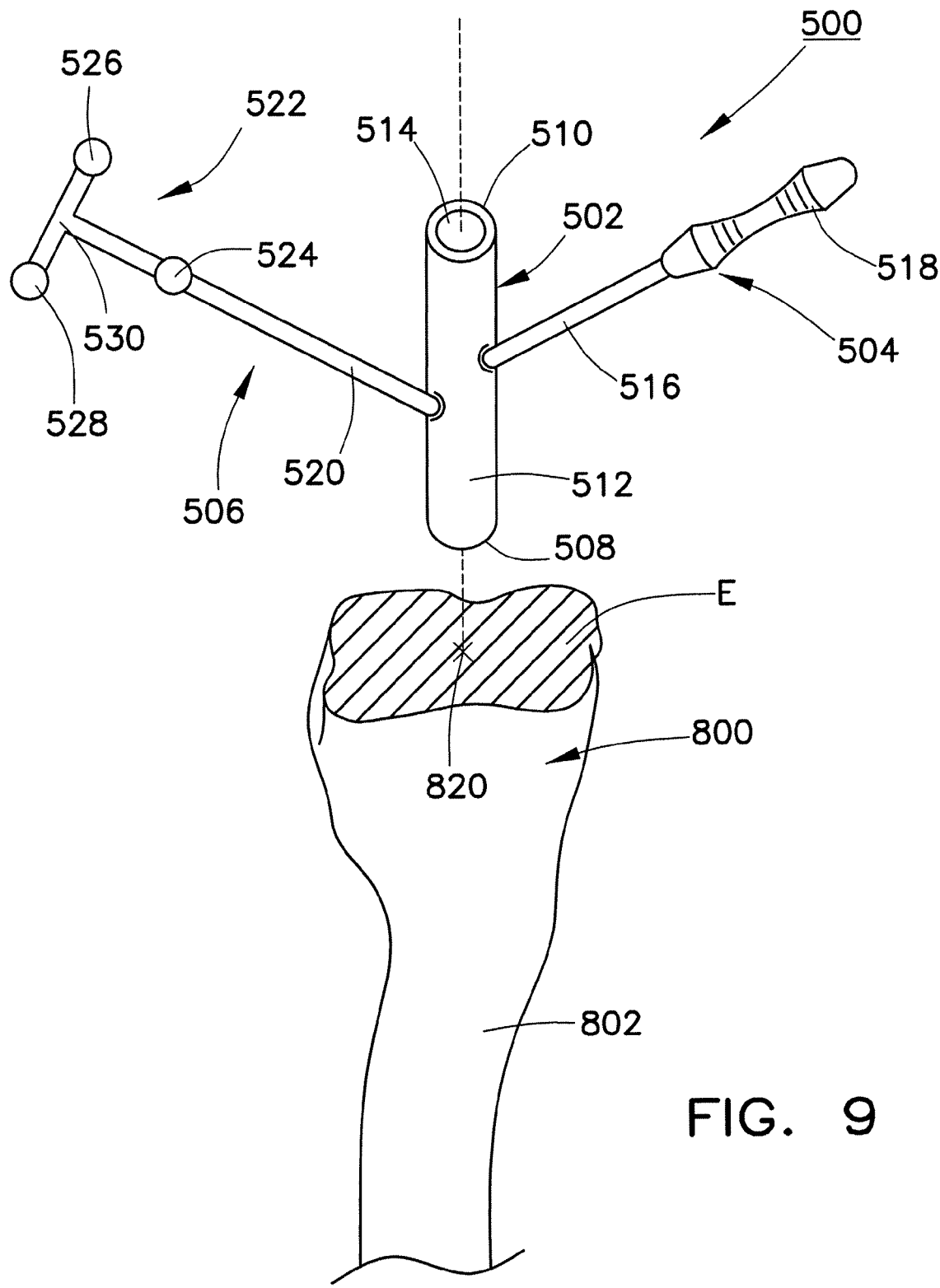
FIG. 9 is a perspective view of the drill cylinder of FIG. 5 being image guided toward a target location on a bone.

Next, depending upon the embodiment of cutting block 100 used, bores may be created in plane E to receive pins extending from cutting block 100 as depicted in FIG. 9. More specifically, drill cylinder 500 is image guided into the desired orientation relative to plane E to create a first bore at a predetermined target location 820 on plane E in the manner described above. Alternatively, the above-described embodiment having image-guidance assembly 506 connected directly to a drill may be used to create the first bore. Location 820 of the first bore corresponds to the desired location of one of mounting locations 127, 129, such as a pin extending from, or provided in place of, bore 131 of attachment wall 132 when cutting block 100 is in its desired position. After the first bore is created, a second bore is created by image guiding drill cylinder 500 (or the drill itself) into a second position as described above. It should be understood, however, that if the selected cutting block embodiment includes bores instead of pins at mounting locations 127, 129, such as cutting block 100 described above, then drill cylinder 500 may be used to insert two pins into plane E, onto which cutting block 100 is placed. Alternatively, after drill cylinder 500 is used to place a first pin into plane E, a first bore, such as bore 131 of cutting block 100 may be placed onto the first pin and rotated (under image guidance) such that second bore 133 of cutting block 100 registers with a second target location (not shown) on plane E. Then, a second pin may be inserted into plane E through cutting block 100. All of these various procedures for mounting cutting block 100 to plane E are performed in a manner similar to that described above with reference to the procedures for mounting cutting block 100 to distal end 802 of femur 800.

Figure 10:
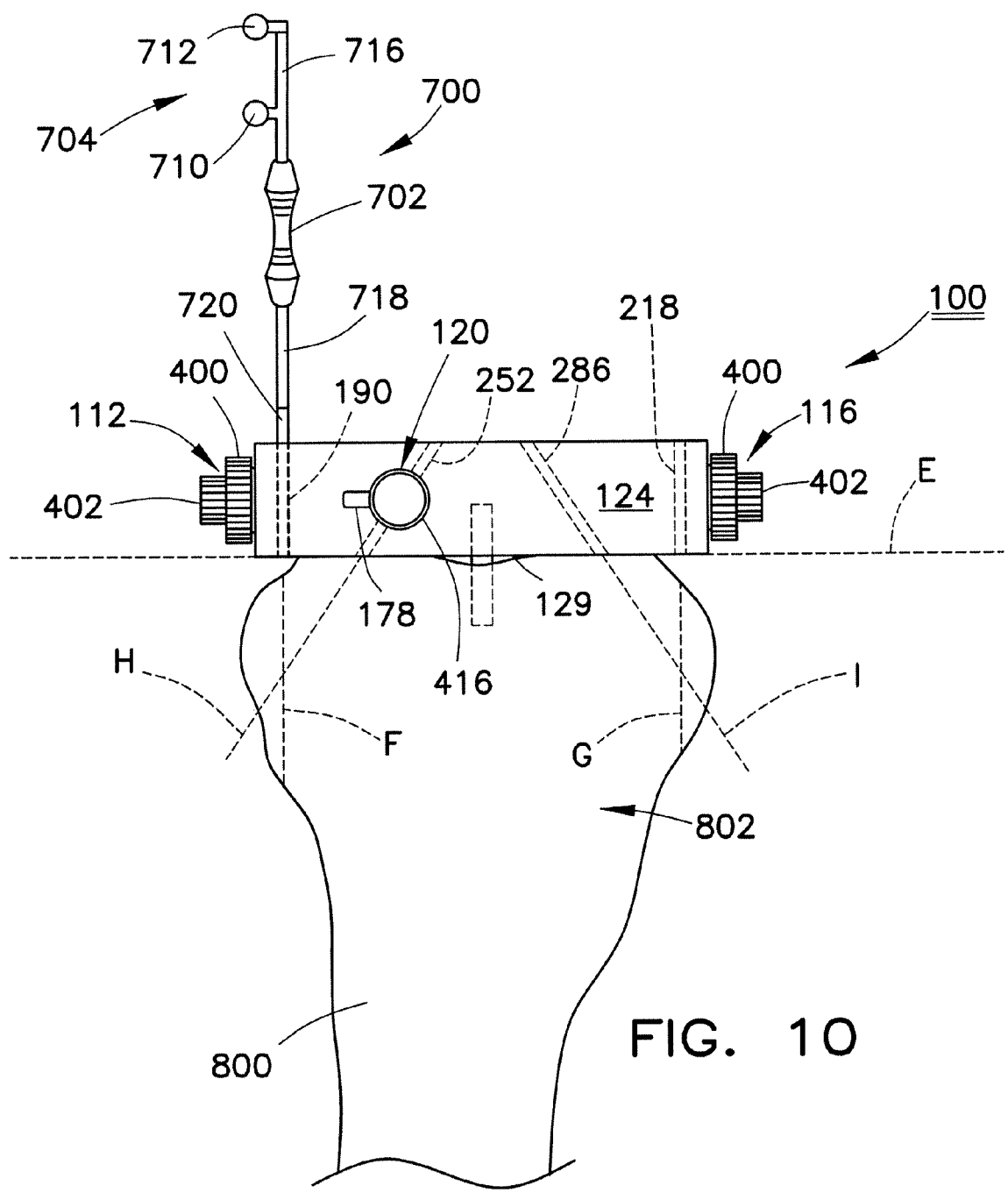
FIG. 10 is a side elevation view of the cutting block of FIG. 1 mounted the distal end of a femur and having a tracking instrument of FIG. 6 mounted thereto.

After cutting block 100 is securely in position on the surface of plane E as shown in FIG. 10, the surgeon may make adjustments to the positions of cutting paths 190, 218, 252, 286 of guides 104-110, respectively, such that they correspond to the desired locations of the four bony cuts needed to facilitate placement of the femoral component of the knee implant. Alternatively, the surgeon may employ the above-described iterative process of making a cut, verifying its location and orientation using tracking instrument 600 or 700, and making a new cut if necessary. Assuming image guided adjustment is employed, the surgeon may place plate 720 of tracking instrument 700 into path 190 of guide 104 to determine its precise location relative to the predetermined desired plane (plane F) of the anterior femoral cut. The surgeon may then adjust the position of path 190 until it corresponds precisely to the desired plane F (as indicated on display 806) by rotating grips 400 of adjustors 112, 114, thereby moving guide 104 toward or away from mounting locations 127, 129. Similarly, tracking instrument 700 may be placed into path 218 of guide 110 to permit image guided adjustment (using grips 400 of adjustors 116, 118 in the manner described above) of the position of path 218 relative to the desired plane of the posterior femoral cut (plane G).

The positions of paths 252, 286 of guides 106, 108, respectively, are adjusted in a similar manner. More specifically, tracking instrument 700 may be placed in path 252 of guide 106 to permit image guided adjustment of the lateral position of path 252 relative to mounting locations 127, 129 using grips 402 of linear adjustors 112, 114 in the manner described above. The angular orientation of path 252 may be adjusted (with tracking instrument 700 still in place) by rotating grip 416 of angular adjustor 120 in the manner described above. When display 806 of image guidance system 808 indicates that the actual orientation of path 252 corresponds to the predetermined desired orientation of the inferior anterior chamfer cut (plane H), guide 106 may be locked in place. The same procedure may be used to perform image guided linear and angular adjustment of path 286 of guide 108 to precisely locate the superior posterior chamfer cut (plane 1).

After paths 190, 218, 252, 286 are adjusted as described above, the surgeon may use a conventional surgical saw (not shown) to create the four bony cuts (in any order) by moving the saw along paths 190, 218, 252, 286. After the cuts are made, cutting block 100 is removed and the femoral component of the knee implant is positioned and secured to distal end 802 of femur 800 in a conventional manner.

As should be apparent from the foregoing, the present system permits accurate placement of cutting block 100 (on distal end 802 of femur 800 and on plane E) through image guidance of drill cylinder 500. Additionally, the system permits the surgeon to even more precisely locate the bony cuts once cutting block 100 is placed by independently adjusting the positions of one or more of paths 190, 218, 252, 286 relative to mounting locations 127, 129, and, in certain circumstances, the angular orientation of path 252, 286 relative to mounting locations 127, 129 in the manner described above. It should be further understood, however, that pre-operative adjustments of paths 190, 218, 252, 286 may be made to simplify the arthroplasty procedure and reduce the time required for the operation.

More specifically, before the operation, the surgeon or a medical technician may determine the size and style of the prosthetic components based upon the physical characteristics of the patient and the surgeon's preferences. The geometric characteristics of the selected components may then be determined by "tracing" the surfaces of the components with, for example, tracking instrument 600. In other words, while tip 620 is moved along the various surfaces of the components, receiver 810 of image guidance system 808 detects the locations of array 604 and processor 811 of system 808 calculates the corresponding locations of tip 620. Processor 811 processes the data representing the surfaces of the components using any of a variety of conventional techniques to generate a three-dimensional model of the component, which is stored in the memory 813 of system 808. Over time, the models generated in this manner may collectively form a library of models. Of course, manufacturers of prosthetic components may provide on a transportable medium (such as a compact disk) data which describes the various styles and sizes of components they sell. This data may be transferred to system 808 and stored in a library of component models, thereby permitting the surgeon or technician to simply select a component from a menu. The stored three-dimensional model of the selected component is then retrieved to facilitate preoperative adjustment of cutting paths 190, 218, 252, 286 of cutting block 100 as described below.

After, for example, the model of the desired femoral component is selected, the surgeon or technician may "trace" the current configuration of cutting block 100 (i.e., the current positions of paths 190, 218, 252, 286 relative to mounting locations 127, 129 of attachment wall 132. Such "tracing" may be performed by placing plate 720 of tracking instrument 700 (or tip 620 of tracking instrument 600) in paths 190, 218, 252, 286 thereby permitting image guidance system 808 to generate a three-dimensional model of cutting block 100. This data, provided to system 808, permits system 808 to generate an image on display 806 comparing the current positions of paths 190, 218, 252, 286 as they relate to the optimal positions for accommodating the known geometry of the selected femoral component. The surgeon or technician may then sequentially place plate 720 of tracking instrument 700 (or tip 620 of tracking instrument 600) into each of paths 190, 218, 252, 286 and adjust the positions of paths 190, 218, 252, 286 using adjustors 112, 114, 116, 118, 120, 122 in the manner described above. Using this technique, the surgeon may use a first cutting block 100 to create the distal femoral cut (plane E). A second cutting block 100 may then be positioned on plane E using drill cylinder 500 as described above, and the locations of paths 190, 218, 252, 286 (which have been pre-adjusted to correspond to the surfaces of the selected femoral component) may simply be verified by placing plate 720 of tracking instrument 700 (or tip 620 of tracking instrument 600) into each of paths 190, 218, 252, 286 and viewing on display 806 the position of each path 190, 218, 252, 286 relative to the desired position. Of course, if less than optimal placement of cutting block 100 is obtained using drill cylinder 500, then adjustments to the positions and/or angular orientations of paths 190, 218, 252, 286 may be desirable during the operation.

Figure 11:
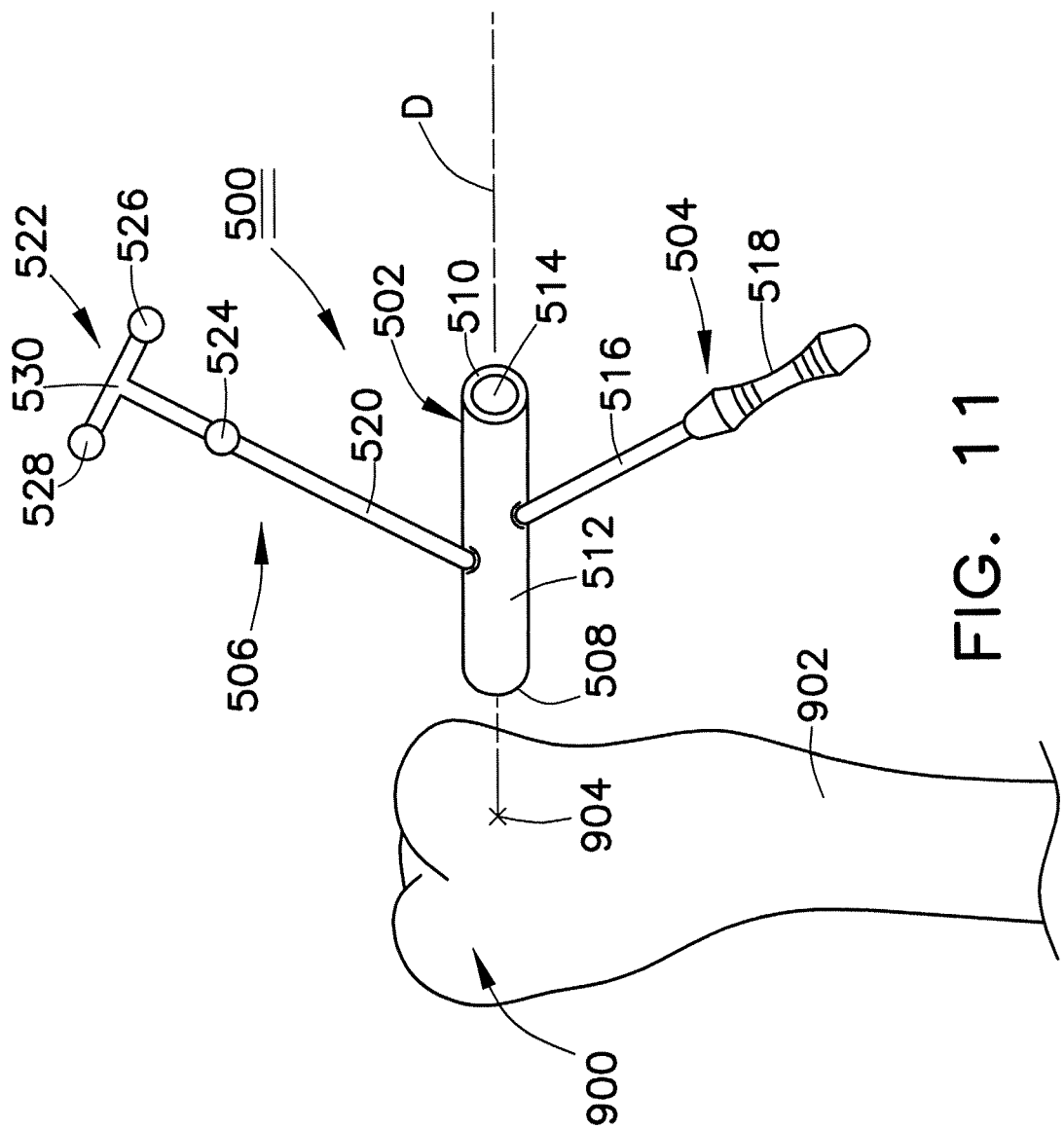
FIG. 11 is a perspective view of the drill cylinder of FIG. 5 being image guided toward a target location on a bone.

The procedure for preparing the proximal end 900 of the tibia 902 to receive a proximal tibial prosthesis (a tibia tray) is generally described with reference to FIGS. 11-13, and is substantially identical to the procedure described above for making the distal femoral cut (plane E). The above-described alternative embodiments including the image-guided drill (as opposed to drill cylinder 500) and the iterative adjustment process (as opposed to image-guided adjustment) have equal application to the following description of shaping tibia 902.

According to one embodiment, image-guided drill cylinder 500 is first moved by the surgeon into a desired or target location 904 on the anterior surface of proximal end 900 of tibia 902 for placing a pin at one of mounting locations 127, 129 (either directly or percutaneously as described above), which in turn locates cutting block 100. More specifically, while viewing a visual indication on display 806 of the three-dimensional orientation of drill cylinder 500 relative to the known structure of tibia 902 (predetermined by "tracing" the surfaces of tibia 902 using tracking instrument 600 in the manner described above), the surgeon moves drill cylinder 500 (either directly or percutaneously) into contact with target location 904 on proximal end 900 of tibia 902. Target location 904 corresponds to the desired location of one of mounting locations 127, 129 (in this example, one of bores 131, 133 formed in attachment wall 132 of cutting block 100). As explained above, image guidance system 808 provides a visual indication on display 806 based on data representing the three-dimensional structure of tibia 902, drill cylinder 500, and cutting block 100. Receiver 810 of image guidance system 808 detects the position of elements 524, 526, 528 of array 522, thereby enabling system 808 to accurately determine the location of end 508 of drill cylinder 500 relative to target location 904. In this manner, the surgeon is able to determine not only whether the point of entry of the pin (not shown) is accurately located, but also whether the angle of entry (represented by axis D in FIG. 11) is appropriate.

Once drill cylinder 500 is accurately placed, an appropriately sized pin is placed into central bore 514 of drill cylinder 500 and screwed or otherwise inserted into target location 904 of tibia 902. The depth of entry of the pin may be controlled using any of a variety of conventional techniques. After the pin is placed, drill cylinder 500 is removed. It should be understood, however, that instead of placing a pin into tibia 902 as described above, drill cylinder 500 may be used to guide a drill bit (not shown) for creating a bore into tibia 902. The depth of entry of the drill bit may similarly be controlled using any of a variety of conventional techniques. After the bore is created and drill cylinder 500 is removed, an appropriately sized pin may be securely inserted into the bore. One of bores 131, 133 of corresponding cutting block 100 in such an embodiment would be sized to securely receive the pin. As yet another alternative, drill cylinder 500 may be used in the manner described above to create a bore in tibia 902 for receiving a pin connected to cutting block 100 at one of mounting locations 127, 129.

Assuming a first pin is placed into the tibia according to the procedure described above, a second pin (not shown) may be placed by repeating the procedure, but placing the second pin at a second target location (not shown) that corresponds to the other of mounting locations 127, 129 (in this example, bores 131, 133) in the known geometry of cutting block 100. After the second pin is inserted into the second target location, drill cylinder 500 is removed. Next, bores 131, 133 of cutting block 100 are positioned onto the first and second pins. As described above, any of a plurality of different techniques may be used to secure cutting block 100 to the pins.

In an alternative embodiment, after the first pin is placed according to the procedure described above, one of bores 131, 133 of cutting block 100 may be placed on the first pin and rotated into position under image guidance such that the other of bores 131, 133 of cutting block 100 registers with the second target location to permit creation of a second bore in proximal end 900 of tibia 902 or insertion of a second pin in the manner described above.

Figure 12:
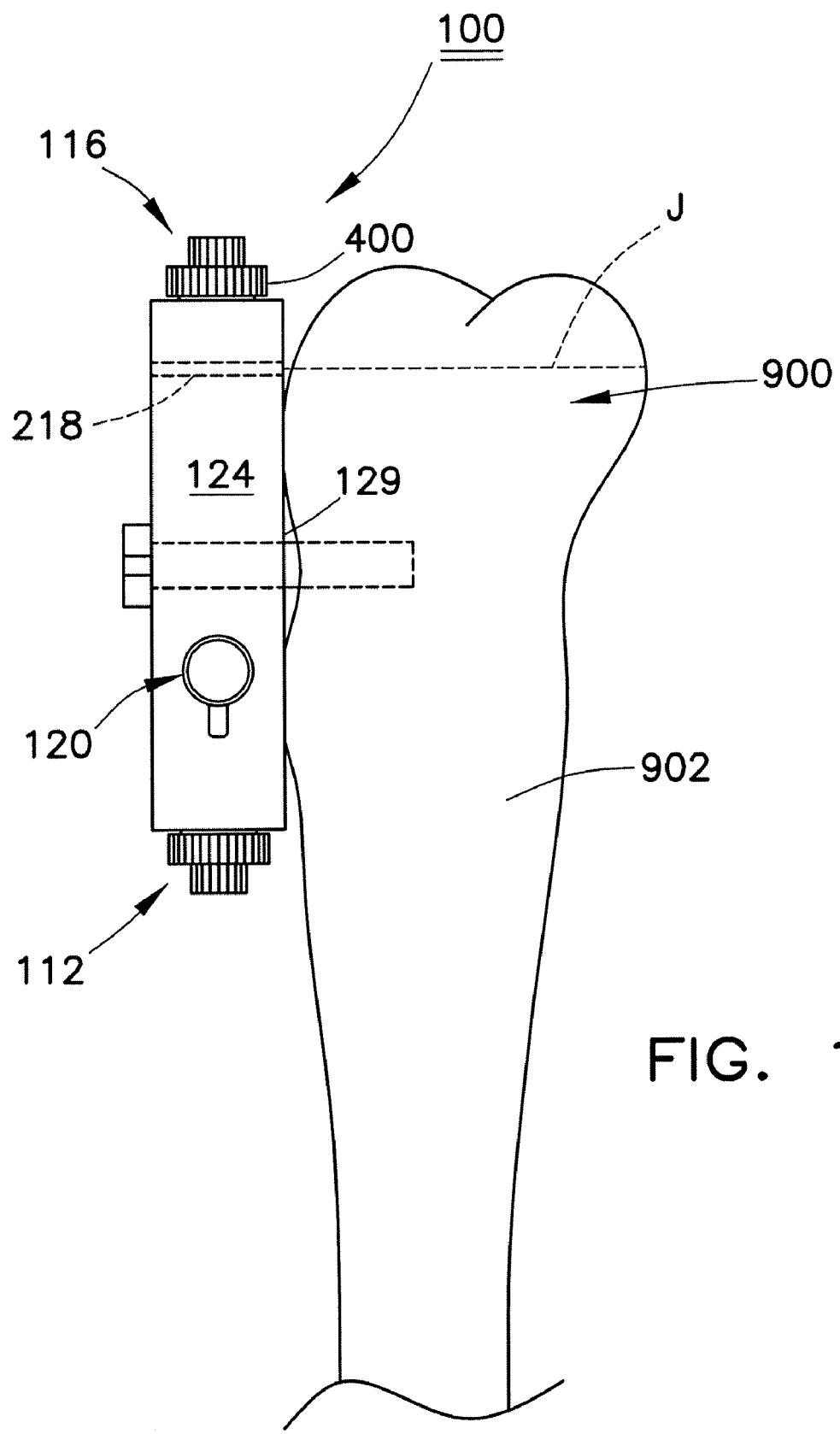
FIG. 12 is a side elevation view of the cutting block of FIG. 1 mounted to a bone in a position to make a proximal tibial cut.

After cutting block 100 is secured on the pins (as shown in FIG. 12), the position of a cutting path, such as path 218, may be adjusted to correspond precisely to the desired orientation of the proximal tibial cut (plane J). Like the femoral cuts described above, the precise orientation of plane J varies based on the geometry of the tibial tray selected, the physical characteristics of the patient, and the preferences of the surgeon. Typically, the medial/lateral orientation of plane J is substantially perpendicular to the tibial mechanical axis, and the anterior/posterior orientation ranges from zero to twelve degrees of posterior slope. The geometry of the selected tibial component is "traced" or otherwise entered into system 808 either during the procedure or pre-operatively as described above. The actual position of path 218 may be determined by placing plate 720 of tracking instrument 700 (or tip 620 of tracking instrument 600) into path 218. System 808 may then process the known geometry of the tibial component, the known geometry of cutting block 100, and the current position of path 218 to provide an image on display 806 to indicate whether path 218 corresponds with sufficient accuracy to the desired location and orientation of plane J. If not, the surgeon may adjust the position of path 218 in the manner described above. Finally, after plane J is created, the surgeon removes cutting block 100.

Figure 13:
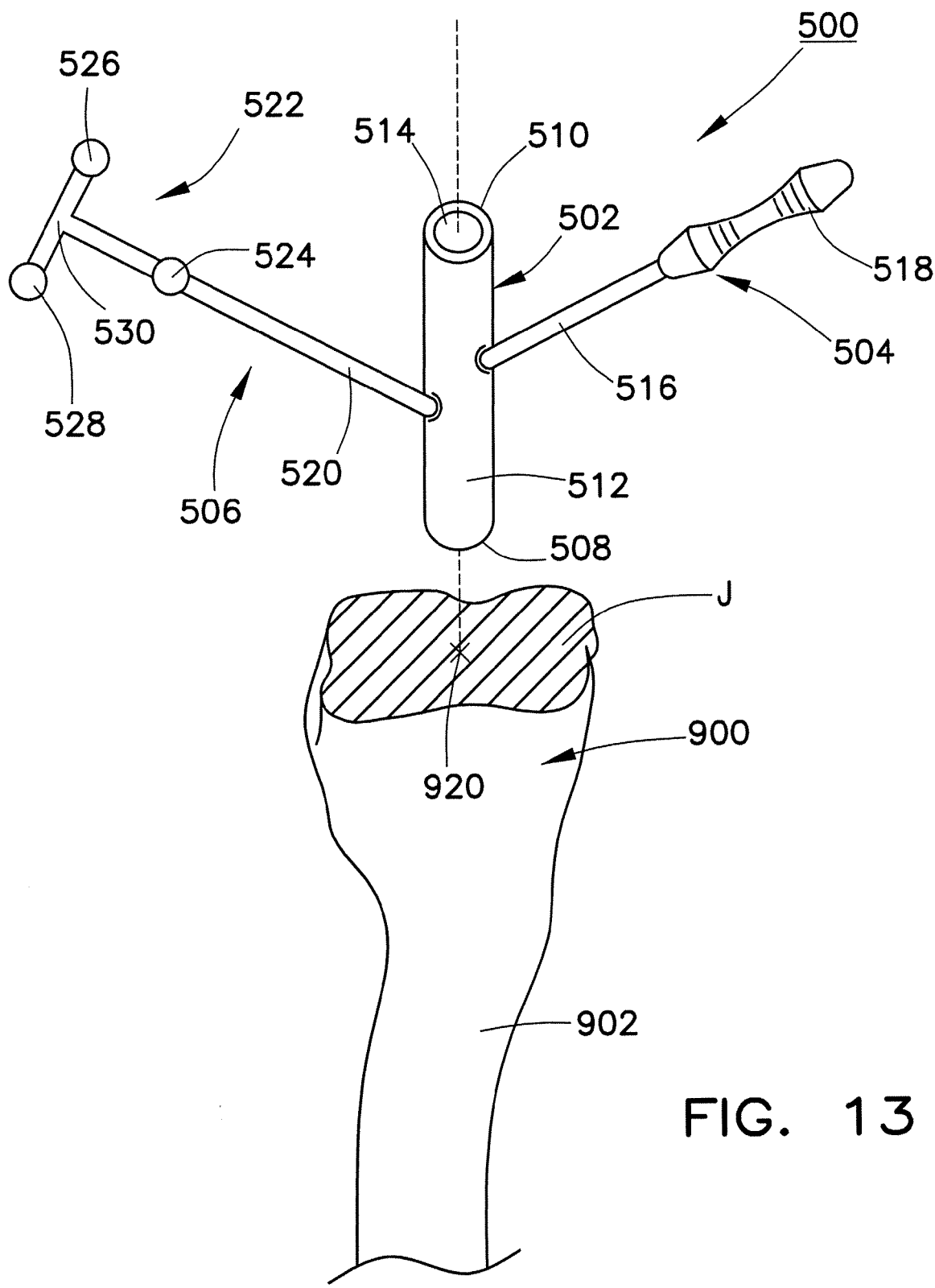
FIG. 13 is a perspective view of the drill cylinder of FIG. 5 being image guided toward a target location on a bone.

Referring now to FIG. 13, the surgeon may next use drill cylinder 500 in the manner described above to accurately locate a bore into plane J at a target location 920 corresponding to a post that typically extends from the tibial component for attachment of the component to tibia 902. Once drill cylinder 500 is accurately located under image guidance, a drill bit (not shown) is passed through central bore 514 to create the bore at target location 920. Finally, drill cylinder 500 is removed, and the surgeon installs and secures the tibial component using any of a variety of conventional techniques. The remaining steps for completion of the arthroplasty procedure do not involve use of the present system.

While the present system has been illustrated and described in detail in the drawings and foregoing description, such illustration and description is to be considered as exemplary and not restrictive in character, it being understood that only exemplary embodiments have been shown and described and that all changes and modifications that come within the spirit of this description and the attached claims are desired to be protected.

What is claimed is:

1. A system for cutting a bone at a desired location, including:
   a drill cylinder having a body that defines a central bore, and an element configured to be detected by an image guidance system to permit image guidance of the drill cylinder to a target location on the bone; and
   a cutting block having
      a frame,
      a first guide adjustably connected to the frame,
      a first adjustor connected to the frame, and
      a first mounting location defined by the frame and configured to attach to the bone at the target location,
      the first guide defining a first cutting path having a position, the position of the first cutting path relative to the first mounting location being adjustable linearly using a grip of the first adjustor,
      a second guide spaced apart from the first guide by a first distance, the second guide being adjustably connected to the frame, and
      a second adjustor connected to the frame,
      the second guide defining a second cutting path having a position, the position of the second cutting path relative to the first cutting path being independently adjustable and the position of the second cutting path relative to the first mounting location being adjustable angularly using a grip of the second adjustor, and
      a third guide spaced apart from the second guide by a second distance and disposed adjacent to and independent thereof, the third guide being adjustably connected to the frame, and
      a third adjustor connected to the frame, the third guide defining a third cutting path having a position, the position of the third cutting path being adjustable using a grip of the third adjustor, being independently adjustable both angularly and linearly with respect to the first cutting path and the second cutting path;
   wherein the spaces between the guides as defined by the first and second distances are independently adjustable with respect to one another.

2. The system of claim 1, wherein the drill cylinder includes a handle connected to the body and configured to permit manual positioning of the body.

3. The system of claim 1, wherein the drill cylinder includes an array of elements configured to be detected by the image guidance system.

4. The system of claim 1, wherein the cutting block frame includes a plurality of channels configured to support the first guide and accommodate movement of the first guide during adjustment of the first cutting path.

5. The system of claim 1, wherein the first guide includes a pair of substantially parallel guide walls extending between a pair of end portions, the guide walls and the end portions defining the first cutting path.

6. The system of claim 1, wherein the first mounting location includes a bore defined by the frame.

7. The system of claim 1, wherein the frame defines a second mounting location, the first mounting location and the second mounting location being located on an attachment wall of the frame.

8. The system of claim 1, wherein the frame further includes a mounting plate coupled to the frame to accommodate linear adjustment of the position of the first cutting path.

9. The system of claim 8, wherein the mounting plate is further configured to accommodate angular adjustment of the first cutting path.

10. The system of claim 9, wherein the mounting plate includes an arcuate channel for supporting a post connected to the first guide, the arcuate channel defining a path of angular adjustment of the first cutting path.

11. The system of claim 1, wherein the position of the second cutting path relative to the first mounting location adjustable linearly.

12. The system of claim 11, wherein the position of the second cutting path relative to the first mounting location is adjustable using a second grip of the first adjustor.

13. The system of claim 1, wherein the frame includes a first end wall, a second end wall, a first side wall extending between the end walls, and a second side wall extending between the end walls.

14. The system of claim 13, wherein the first guide is connected between the side walls adjacent the first end wall.

15. The system of claim 14, wherein the second guide is adjustably connected to the frame between the side walls.

16. The system of claim 15, wherein the third guide is adjustably connected to the frame between the side walls.

17. The system of claim 16, wherein the cutting block further includes a fourth guide defining a fourth cutting path, the fourth guide being adjustably connected to the frame between the side walls adjacent the second end wall.

18. The system of claim 17, wherein the second guide and the third guide are positioned between the first guide and the fourth guide.

19. The system of claim 18, wherein the second guide is positioned between the first guide and the first mounting location and the third guide is positioned between the fourth guide and the first mounting location.

20. The system of claim 1, wherein the position of first guide is adjustable linearly relative to the first mounting location using the first adjustor.

21. The system of claim 17, wherein the cutting block further includes a fourth adjustor, a first guide and the second guide being adjustable linearly relative to the first mounting location using the first adjustor, the third guide and the fourth guide being adjustable linearly relative to the first mounting location using the third, and the third guide being adjustable angularly relative to the first mounting location using the fourth adjustor.

22. The system of claim 1, further including a tracking instrument having an engagement portion and an element configured to be detected by the image guidance system to permit image guidance of adjustments of the first cutting path relative to the first mounting location when the engagement portion is placed in engagement with the first cutting path.

23. The system of claim 22, wherein the tracking instrument includes a plurality of elements configured to be detected by the image guidance system.

24. The system of claim 22, wherein the engagement portion includes a plate configured to fit within the first cutting path.

25. The system of claim 22, wherein the engagement portion includes a tip positioned at an end of the tracking instrument that is substantially opposite the element.

26. A system for locating a planar cut through a portion of a bone, including:
   an image guided drill cylinder having a body that defines a central bore configured to receive one of a drill bit and a pin, and a tracking element coupled to the body;
   a receiver configured to sense a present location of the tracking element and provide location signals representing the present location of the tracking element;
   a processor coupled to the receiver, the processor being configured to receive the location signals and to determine, based upon the location signals and data representing a target location on the bone, a present location of the central bore relative to the target location;
   a display coupled to the processor, the display being configured to generate images representing the present location of the central bore relative to the target location so that the drill cylinder may be moved until the present location of the central bore registers with the target location; and
   a cutting block having a frame including a first mounting location configured to connect the cutting block to the bone at the target location, and a first guide adjustably mounted to the frame for movement relative to the first mounting location, the first guide defining a first cutting path adapted to guide a saw for creating the planar cut when the first guide is adjusted such that the first cutting path is in a position corresponding to the planar cut, a second guide spaced apart from the first guide by a first distance and defining a second cutting path having a position, the position of the second cutting path relative to the first mounting location being adjustable angularly and linearly with respect to the first cutting path, and a third guide spaced apart from the second guide by a second distance and adjacent the second guide and independent of the first and the second guides, the third guide defining a third cutting path angularly adjustable with respect to the first guide and the second guide;
   wherein the spaces between the guides as defined by the first and second distances are independently adjustable with respect to one another.

27. The system of claim 26, wherein the cutting block frame includes a pair of channels positioned to support the first guide during adjustment of the first cutting path.

28. The system of claim 26, wherein the first guide includes a pair of guide walls substantially defining the first cutting path.

29. The system of claim 26, wherein the frame defines a second mounting location, the first mounting location and the second mounting locations being located on an attachment wall of the frame.

30. The system of claim 26, wherein the frame further includes a mounting plate coupled to the frame to accommodate linear adjustment of the position of the first cutting path.

31. The system of claim 30, wherein the mounting plate is further configured to accommodate angular adjustment of the second cutting path.

32. The system of claim 26, wherein the cutting block further includes a second adjustor having a grip, use of the second adjustor grip causing angular adjustment of the position of the second cutting path.

33. The system of claim 26, wherein the cutting block further includes a fourth guide defining a fourth cutting path, the fourth guide being adjustably connected to the frame.

34. The system of claim 33, wherein the second guide is positioned between the first guide and the first mounting location and the third guide is positioned between the fourth guide and the first mounting location.

35. The system of claim 33, wherein the first guide is adjustable linearly relative to the first mounting location using a first adjustor having a grip.

36. The system of claim 35, wherein the cutting block further includes a second adjustor, a third adjustor, and a fourth adjustor, the first guide and the second guide being adjustable linearly relative to the first mounting location using the first adjustor, the second guide being adjustable angularly relative to the first mounting location using the second adjustor, the third guide and the fourth guide being adjustable linearly relative to the first mounting location using the third adjustor, and the third guide being adjustable angularly relative to the first mounting location using the fourth adjustor.

37. The system of claim 26, further including a tracking instrument having an engagement portion and an element configured to be detected by the receiver to permit image guidance of adjustments of the first cutting path relative to the first mounting location when the engagement portion is placed in engagement with the first cutting path.

38. The system of claim 37, wherein the engagement portion includes a plate configured to fit within the first cutting path.

39. A cutting block configured to guide a cutting instrument during a bone cutting procedure, including:
   a frame;
   a first mounting location defined by a portion of the frame;
   a first guide coupled to the frame, the first guide including a first surface defining a first cutting path;
   a second guide spaced apart from the first guide by a first distance and coupled to the frame, the second guide including a second surface defining a second cutting path;
   a first adjustor coupled to the first guide, the first adjustor including a first grip configured to permit a user to actuate the first adjustor, thereby causing linear movement of at least a portion of the first cutting path relative to the first mounting location;
   a first adjustor coupled to the first guide, the first adjustor including a first grip configured to permit a user to linearly actuate the first adjustor, thereby causing linear movement of at least a portion of the first cutting path relative to the first mounting location;
   a second adjustor coupled to the second guide, the second adjustor including a first grip configured to permit a user to angularly actuate the second adjustor, thereby causing angular movement of the second cutting path relative to the first mounting location and to the first guide;

a third guide spaced apart from the second guide by a second distance and coupled to the frame, the third guide including a third surface defining a third cutting path and being independent of the first guide and the second guide; and a third adjustor coupled to the third guide, the third adjustor including a first grip configured to permit a user to linearly actuate the third adjustor thereby causing linear movement of at least a portion of the third cutting path relative to the first mounting location;

wherein the spaces between the guides as defined by the first and second distances are independently adjustable with respect to one another.

40. The cutting block of claim 39, wherein the frame includes a first pair of channels configured to support the first guide and accommodate movement of the first guide during adjustment of the first cutting path, and a second pair of channels configured to support the second guide and accommodate movement of the second guide during adjustment of the second cutting path.

41. The cutting block of claim 39, wherein the first guide includes a guide wall extending between a pair of end portions, the first surface being disposed on the guide wall.

42. The cutting block of claim 39, wherein the frame defines a second mounting location, the first mounting location and the second mounting locations being located on an attachment wall of the frame.

43. The cutting block of claim 39, wherein the frame further includes a mounting plate coupled to the frame to accommodate linear adjustment of the position of the second cutting path relative to the first mounting location.

44. The cutting block of claim 43, wherein the mounting plate includes an arcuate channel configured to accommodate angular adjustment of the second cutting path.

45. The cutting block of claim 39, wherein the position of the second cutting path relative to the first mounting location is adjustable using a second grip of the first adjustor.

46. The cutting block of claim 45, wherein use of the second grip causes linear adjustment of the position of the second cutting path.

47. The cutting block of claim 39, wherein the frame includes a first end wall, a second end wall, and a pair of substantially parallel side walls extending between the end walls.

48. The cutting block of claim 47, wherein the third guide is adjustably connected to the frame between the side walls.

49. The cutting block of claim 48, wherein the cutting block further includes a fourth guide defining a fourth cutting path, the fourth guide being adjustably connected to the frame between the side walls adjacent the second end wall.

50. The cutting block of claim 49, wherein the second guide is positioned between the first guide and the first mounting location and the third guide is positioned between the fourth guide and the first mounting location.

51. A system for cutting a bone at a desired location, including:

a drill;

an element attached to the drill and configured to be detected by an image guidance system to permit image guidance of a drill bit connected to the drill to a target location on the bone; and a cutting block having
a frame,
a first guide adjustably connected to the frame,
a first adjustor connected to the frame,
a first mounting location defined by the frame and configured to attach to the bone at the target location,
the first guide defining a first cutting path having a position, the position of the first cutting path relative to the first mounting location being adjustable linearly using a grip of the first adjustor,
a second guide spaced apart from the first guide by a first distance, the second guide being adjustably connected to the frame and independent of the first guide,
a second adjustor connected to the frame,
the second guide defining a second cutting path having a position, the position of the second cutting path relative to the first mounting location being adjustable angularly using a grip of the second adjustor and linearly using the first guide, and
a third guide spaced apart from the second guide by a second distance and adjustably connected to the frame and independent of the first guide and the second guide,
a third adjustor connected to the frame,
a fourth adjustor connected to the frame,
the third guide defining a third cutting path having a position, the position of the third cutting path relative to the first mounting location being adjustable angularly using a grip of the fourth adjustor and linearly using a grip of the third adjustor;
wherein the spaces between the guides as defined by the first and second distances are independently adjustable with respect to one another.

52. A system for locating a plurality of planar cuts through a bone, including:

means for image guiding a drill to create a bore in a target location of the bone;

means for providing first, second, and third cutting paths to guide a saw for creating the plurality of planar cuts;

means for mounting the providing means to the bone at the target location;

means for image guiding the providing means; and means for adjusting a position of the providing means relative to the mounting means, the means for adjusting including a means to adjust the first cutting path linearly, the second cutting path angularly and linearly, and the third cutting path angularly and linearly, wherein each of the means to adjust the first cutting path, the second cutting path and the third cutting path can be adjusted independently of each of the other means to adjust;

wherein the providing means includes first, second and third guides, the second guide being spaced apart from the first guide by a first distance and the third guide being spaced apart from the second guide by a second distance and wherein the spaces between the guides, as defined by the first and second distances, are independently adjustable with respect to one another.

* * * * *

UNITED STATES PATENT AND TRADEMARK OFFICE
CERTIFICATE OF CORRECTION

PATENT NO. : 7,641,660 B2
APPLICATION NO. : 10/795891
DATED : January 5, 2010
INVENTOR(S) : Ryan Cameron Lakin et al.

It is certified that error appears in the above-identified patent and that said Letters Patent is hereby corrected as shown below:

In claim 8, line 24, please replace the term "first" with the term "second"

In claim 9, line 27, please replace the term "first" with the term "second"

In claim 10, line 30, please replace the term "first" with the term "second"

In claim 10, line 31, please replace the term "first" with the term "second"

In claim 11, line 34, please insert the term --is-- before the term "adjustable"

In claim 21, line 64, please replace the second occurrence of the term "a" with the term "the"

In claim 21, line 1 of column 17, please insert the term --adjuster-- after the first occurrence of the term "third"

In claim 26, line 42, please delete the term "and"

In claim 30, line 7, please replace the term "first" with the term "second"

In claim 39, lines 60-64, please delete the duplicate phrase "a first adjustor coupled to the first guide, the first adjustor including a first grip configured to permit a user to linearly actuate the first adjustor, thereby causing linear movement of at least a portion of the first cutting path relative to the first mounting location"

Signed and Sealed this

Sixteenth Day of February, 2010

David J. Kappos
*Director of the United States Patent and Trademark Office*

UNITED STATES PATENT AND TRADEMARK OFFICE
CERTIFICATE OF CORRECTION

PATENT NO.         : 7,641,660 B2                                             Page 1 of 1
APPLICATION NO.    : 10/795891
DATED              : January 5, 2010
INVENTOR(S)        : Ryan Cameron Lakin et al.

It is certified that error appears in the above-identified patent and that said Letters Patent is hereby corrected as shown below:

Column 16, In claim 8, line 24, please replace the term "first" with the term "second"

Column 16, In claim 9, line 27, please replace the term "first" with the term "second"

Column 16, In claim 10, line 30, please replace the term "first" with the term "second"

Column 16, In claim 10, line 31, please replace the term "first" with the term "second"

Column 16, In claim 11, line 34, please insert the term --is-- before the term "adjustable"

Column 16, In claim 21, line 64, please replace the second occurrence of the term "a" with the term "the"

In claim 21, line 1 of column 17, please insert the term --adjuster-- after the first occurrence of the term "third"

Column 17, In claim 26, line 42, please delete the term "and"

Column 18, In claim 30, line 7, please replace the term "first" with the term "second"

Column 18, In claim 39, lines 60-64, please delete the duplicate phrase "a first adjustor coupled to the first guide, the first adjustor including a first grip configured to permit a user to linearly actuate the first adjustor, thereby causing linear movement of at least a portion of the first cutting path relative to the first mounting location"

This certificate supersedes the Certificate of Correction issued February 16, 2010.

Signed and Sealed this

Twenty-third Day of March, 2010

David J. Kappos
*Director of the United States Patent and Trademark Office*